(12) United States Patent
Jung et al.

(10) Patent No.: US 7,301,636 B2
(45) Date of Patent: Nov. 27, 2007

(54) MINIATURIZED SYSTEM AND METHOD FOR MEASURING OPTICAL CHARACTERISTICS

(75) Inventors: Wayne D. Jung, Morton Grove, IL (US); Russell W. Jung, Morton Grove, IL (US); Walter W. Sloan, Lake Bluff, IL (US); Alan R. Loudermilk, Chicago, IL (US)

(73) Assignee: Vita Zahnfabrik H. Rauter GmbH & Co. KG (DE)

( * ) Notice: Subject to any disclaimer, the term of this patent is extended or adjusted under 35 U.S.C. 154(b) by 286 days.

(21) Appl. No.: 10/923,647

(22) Filed: Aug. 19, 2004

(65) Prior Publication Data

US 2005/0083526 A1   Apr. 21, 2005

Related U.S. Application Data

(63) Continuation-in-part of application No. PCT/US03/05310, filed on Feb. 21, 2003, which is a continuation of application No. 10/081,879, filed on Feb. 21, 2002, now Pat. No. 6,903,813.

(51) Int. Cl.
*G01J 3/46* (2006.01)

(52) U.S. Cl. .................. 356/402; 433/203.1; 433/215; 433/26; 356/425; 356/405

(58) Field of Classification Search ............. 356/402, 356/405, 425, 73; 250/910; 433/203.01, 433/215
See application file for complete search history.

(56) References Cited

U.S. PATENT DOCUMENTS

| | | | | |
|---|---|---|---|---|
| 6,037,629 A | * | 3/2000 | Gardner et al. | ............. 257/333 |
| 6,512,577 B1 | * | 1/2003 | Ozanich | ...................... 356/73 |

* cited by examiner

*Primary Examiner*—Layla G. Lauchman
(74) *Attorney, Agent, or Firm*—Christie, Parker & Hale, LLP.

(57) ABSTRACT

A miniaturized spectrometer/spectrophotometer system and methods are disclosed. A probe tip including one or more light sources and a plurality of light receivers is provided. A first spectrometer system receives light from a first set of the plurality of light receivers. A second spectrometer system receives light from a second set of the plurality of light receivers. A processor, wherein the processor receives data generated by the first spectrometer system and the second spectrometer system, wherein an optical measurement of a sample under test is produced based on the data generated by the first and second spectrometer systems. Improved shade matching/prediction results are obtained through the use of volumes/regions, preferably polygons, around shades in a shade system.

20 Claims, 24 Drawing Sheets

LCH Shade matching

Determining if a point is inside a polygon

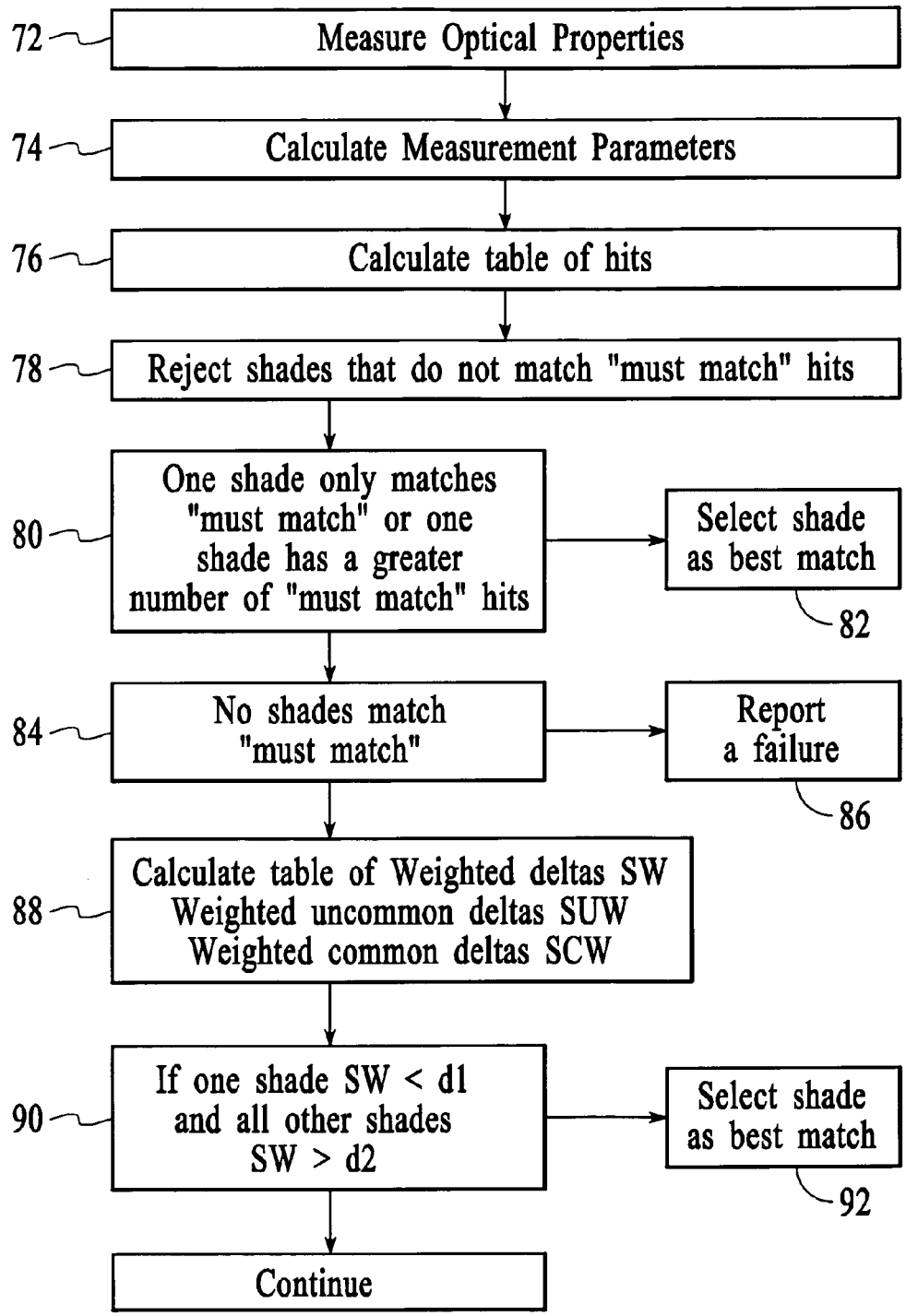
FIG.11/1

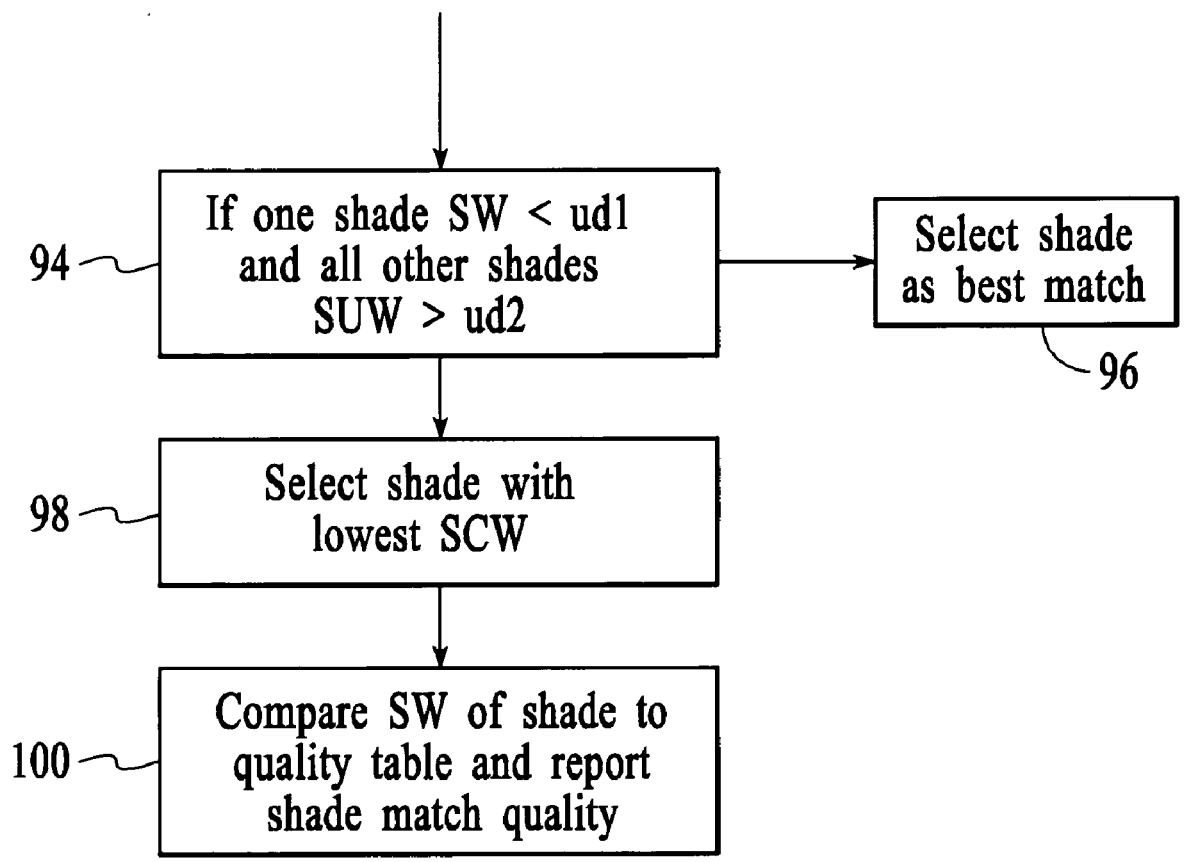
FIG.11/2

LCH Shade matching

Determining if a point is inside a polygon

Determining if a polygon line is crossed

Shortest distance to a line segment

Shortest distance to a line segment

Classical          3D Master

A1                 2M2

Vita Classical and 3D shade match reporting for no
Classical neighbors and non-interpolated 3D shade

FIG.18A

Classical          3D Master

A1                 2.5M2.5
A2  B2

Shade reporting for Classical and 3D shades showing
neighbors for Classical shades and interpolation for 3D shades

FIG.18B

MINIATURIZED SYSTEM AND METHOD FOR MEASURING OPTICAL CHARACTERISTICS

This application is a continuation in part of PCT App. Ser. No. PCT/US03/05310 filed on 21 Feb. 2003, which is a continuation in part of U.S. application Ser. No. 10/081,879, filed on 21 Feb. 2002 now U.S. Pat. No. 6,903,813, both of which are hereby incorporated by reference.

FIELD OF THE INVENTION

The present invention relates to devices and methods for measuring optical characteristics such as color spectrums, translucence, gloss, and other characteristics of objects such as teeth, and more particularly to devices and methods for measuring the color and other optical characteristics of teeth, fabric or numerous other objects, materials or surfaces. In particular, the present invention relates to improved shade matching/prediction.

BACKGROUND OF THE INVENTION

A need has been recognized for devices and methods of measuring the color or other optical characteristics of teeth and other objects, particularly in the field of dentistry. Reference is made to the following applications, all by inventors hereof, which are hereby incorporated by reference, which disclose various systems and methods for measuring teeth and other objects: U.S. application Ser. No. 09/091,208, filed on Jun. 8, 1998, which is based on International Application No. PCT/US97/00126, filed on Jan. 2, 1997, which is a continuation in part of U.S. application Ser. No. 08/581,851, now U.S. Pat. No. 5,745,229, issued Apr. 28, 1998, for Apparatus and Method for Measuring Optical Characteristics of an Object; U.S. application Ser. No. 09/091,170, filed on Jun. 8, 1998, which is based on International Application No. PCT/US97/00129, filed on Jan. 2, 1997, which is a continuation in part of U.S. application Ser. No. 08/582,054, now U.S. Pat. No. 5,759,030 issued Jun. 2, 1998, for Apparatus and Method for Measuring Optical Characteristics of Teeth; PCT application Ser. No. PCT/US98/13764, filed on Jun. 30, 1998, which is a continuation in part of U.S. application Ser. No. 08/886,223, filed on Jul. 1, 1997, for Apparatus and Method for Measuring Optical Characteristics of an Object; PCT Application No. PCT/US98/13765, filed on Jun. 30, 1998, which is a continuation in part of U.S. application Ser. No. 08/886,564, filed on Jun. 30, 1998, for Apparatus and Method for Measuring Optical Characteristics of Teeth; and U.S. application Ser. No. 08/886,566, filed on Jul. 1, 1997, for Method and Apparatus for Detecting and Preventing Counterfeiting. The foregoing patent documents and those upon which this application claims priority are sometimes referenced collectively herein as the "Referenced Patent Documents."

The foregoing patent documents disclose a variety of systems and methods for measuring teeth and other objects. For example, FIG. 1 of U.S. Pat. No. 5,880,826 discloses a system that uses a pen-like probe that could be held much like a pencil with the probe tip directed to the tooth or other object. FIG. 35 of U.S. Pat. No. 5,880,826 discloses a handheld configuration which may be held much like a gun, with a switch located in a position for the "trigger function" to activate the system. One color measuring system introduced to the market has a physical configuration in which the user holds the instrument "football style" (the user's hand cradles the instrument much like a user would hold a football in a traditional football throwing motion). In general, in the field of dentistry a variety of stylus, probe, gun-like and other implements have been proposed and/or utilized to varying degrees of commercial acceptance.

Although the systems described in the Referenced Patent Documents, and the above mentioned dental implements, provide a variety of physical arrangements for dental instruments, there is still a need, particularly with respect to instruments that are capable of quantifying the optical properties of dental objects such as teeth, for instruments that are easier to hold and utilize in the dental or similar environment as compared with such existing physical arrangements. In particular, there is a need for instruments of improved physical construction so that dentists and other users may measure teeth and other objects comfortably and precision, and preferably without bending or contorting the wrist, hand or other body parts.

There also continues to be a need for such instruments with improved infection prevention implements, and for such instruments that utilize multiple spectrometers to more optimally measure and quantify the optical properties of translucent, pearlescent or other optically complex materials.

SUMMARY OF THE INVENTION

The present invention provides a new and improved physical arrangement, particularly for a spectrometer or spectrophotometer-based instrument, that facilitates the measurement of optical properties of teeth and other dental and other objects and materials.

In accordance with the present invention, a housing encloses a spectrometer or spectrophotometer; preferably multiple spectrometers are utilized in order to measure multiple spectrums (preferably simultaneously) of light received from the object under test. The housing includes a body portion that preferably houses the spectrometer(s) or spectrophotometer(s) (herein, a spectrophotometer generally consists of a spectrometer and light source, and perhaps a power source such as a battery). The spectrometer assembly preferably is located in the palm of the user's hand. Extending from, and preferably integral with, the body portion is neck portion. Extending from, and preferably integral with, the neck portion is a tip portion. Optics, such as light guiding fiber optics or the like, preferably carry light to a probe tip at an end of the portion, at which point the light leaves the instrument in order to illuminate the tooth or other object or material, and return the light to the spectrometer(s) for analysis.

In accordance with preferred embodiments, the neck portion is configured to have an upper portion that includes a location for placement of a user's index finger. This location may have an indenture or other textured area or friction surface (such as small bumps, a rubber surface or the like that tends to increase the friction between the user's index finger and the instrument) such that a user's index finger may be securably be positioned at that location. With the user's index finger reliably positioned at such a location on the neck portion, the tip portion of the instrument may be more precisely moved towards a desired or predetermined location on the tooth or other object so that the tip may measure the desired or predetermined location.

Also in accordance with preferred embodiments, one or a plurality of switches are provided for activation and/or control of the instrument, preferably located and operated in a manner such that the measurement is not adversely affected by undesired movement induced by the switch activation. One or more switches may be located in a position where an index finger is positioned during use of the instrument. Alternatively, one or more switches may be located on a lower surface of the body portion such that the switch may be activated by a squeezing motion of one or more of the user's fingers, while not pulling the instrument away from the desired or predetermined location on the tooth or other object. In addition (or alternatively), the tip may move respect to other parts of the tip portion or the neck and body portion such that the movement of the tip may be detected electrically, mechanically or optically.

An improved barrier infection control implement also is preferably utilized in accordance with the present invention. Preferably, a pliant, stretchy, transparent material fully encases and covers the tip portion of the instrument. In preferred embodiments, an inner surface of the infection control implement is relatively smooth or "satinized" in order to facilitate guiding the tip portion of the instrument into the infection control implement, and an outer surface of the infection control implement has a degree of tackiness or stickiness, particularly as compared to the inner surface, such that upon contact with the object under evaluation the tip portion mildly adheres to the surface of the object. With such an outer surface, measurement of objects such as teeth are facilitated, as the tip of the instrument may be directed to a desired spot of the object for evaluation, with the stickiness, or "non-slippery-ness," of the outer surface of the infection control implement serving to prevent movement of the tip from the desired spot on the object. Preferably, a calibration measurement of a material of known or predetermined optical characteristics serve to calibrate out any optical effect introduced by the infection control implement. Such a calibration measurement preferably is conducted at instrument powerup, prior to taking actual measurements, at periodic or other suitable intervals. Such a calibration measurement also serves to normalize the instrument and calibrate out effects due to lamp drift, aging of fiber optics, optical couplers, filters and other optical components and the like, as well as to normalize the electronics and produce a "black level," such as described in the previously referenced patent documents.

Accordingly, it is an object of the present invention to provide an improved spectrometer/spectrophotometer, and/or housing arrangement for a spectrometer or spectrophotometer, particularly for the field of dentistry.

It is another object of the present invention to provide an improved spectrometer/spectrophotometer, and/or housing arrangement for a spectrometer or spectrophotometer, particularly having a body portion that encloses the spectrometer or spectrometer and fits in the user's hand during operation of the instrument.

It is yet another object of the present invention to provide an improved spectrometer/spectrophotometer, and/or housing arrangement for a spectrometer or spectrophotometer, particularly having a neck portion with an index finger placement location.

It is still another object of the present invention having one or more switches that activate or control the instrument and are arranged, such as with a moveable tip, located on an under side of the body portion, such that the one or more switches may be operated while not having the act of activating the switch induce undesired movement of the instrument.

It is yet another object of the present invention to provide an improved instrument for, and methods of making, optical measurements utilizing a plurality of spectrometers or other color measuring devices in order to quantify optical properties of materials that may be translucent, pearlescent or otherwise optically complex; particular example being human teeth and restorative dental materials, gems, multi-layered painted articles and the like.

It is an object of the present invention to provide such an instrument that may be utilized with a barrier infection or contamination control implement, which preferably has a smooth inner surface and a slip-resistant outer surface, the inner surface of which preferably serves to facilitate insertion of the instrument's probe tip into the infection or contamination control implement, and the outer surface of which preferably facilitates measurement of the object under evaluation by providing a probe tip surface that tends not to slip during from the desired measurement spot during the optical measurement.

It is another object of the present invention to provide a shade matching system and method in which parameters in addition to, or other than, a $\Delta E$ calculation in order to shade match teeth, such as combinations of tristimulus parameters; in accordance with embodiments of the present invention, one set of parameters may be advantageously utilized for some shades, while another set of parameters may be advantageously utilized to resolve other shades; such embodiments may be particularly useful when different combinations are used in situations where the shades do not evenly cover color space.

It is yet another object of the present invention to provide a shade matching system that can be easily programmed to run on a microprocessor in situ in a short period of time.

It is another object of the present invention to provide a shade matching algorithm that more optimally matches human vision.

It is yet another object of the present invention to provide an algorithm that accounts for variation in color reference standards.

Finally, it is an object of the present invention to provide improved shade matching algorithms based on the polygons.

BRIEF DESCRIPTION OF THE DRAWINGS

The above objects and other advantages of the present invention will become more apparent by describing in detail the preferred embodiments of the present invention with reference to the attached drawings in which:

FIG. 11 is a flow chart illustrating a best shade determination process flow in accordance with certain embodiments of the present invention;

FIGS. 14-18B illustrate improved shade matching/prediction and reporting preferably based on the use of polygons.

DETAILED DESCRIPTION OF THE PREFERRED EMBODIMENTS

The present invention will be described in greater detail with reference to certain preferred and alternative embodiments. As described below, refinements and substitutions of the various embodiments are possible based on the principles and teachings herein.

Figure 1:
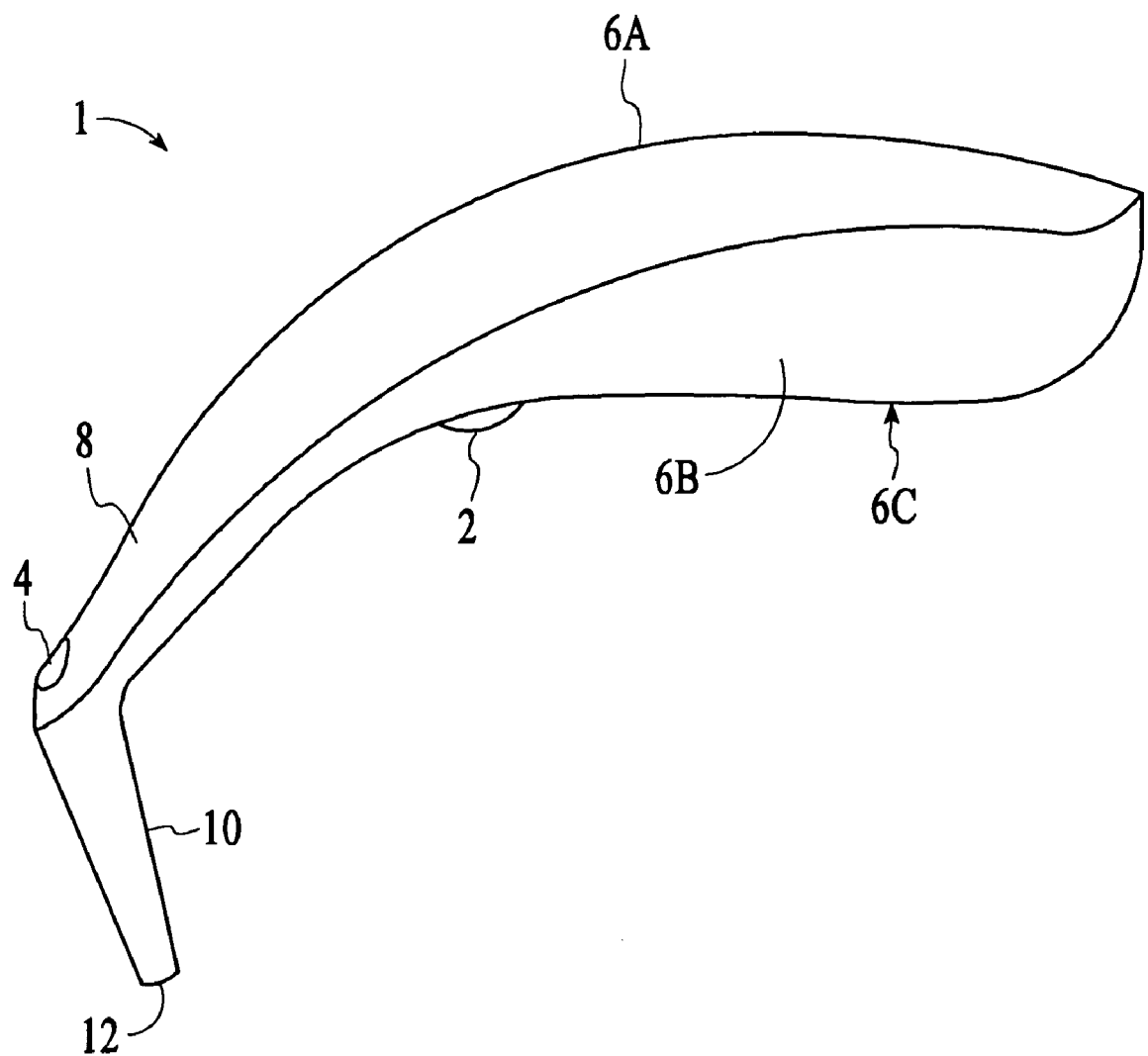
FIG. 1 is an overview of a spectrometer/spectrophotometer housing arrangement in accordance with an exemplary preferred embodiment of the present invention.

FIG. 1 is an overview of a spectrometer/spectrophotometer housing arrangement in accordance with an exemplary preferred embodiment of the present invention. As illustrated, spectrometer/spectrophotometer 1 in accordance with preferred embodiments preferably includes a housing includes body portion 6A and 6B that preferably houses the spectrometer or spectrophotometer (herein, the spectrophotometer generally consisting of a spectrometer and light source, and perhaps a power source such as a battery, while a spectrometer embodiment may provide light that is provided via an optical cable from an external light source). In the illustrated embodiment, the body portion 6A/6B consists of two parts, upper portion 6A and lower portion 6B, the two portions of which together define the body portion, and in the preferred embodiment the neck portion. Such a two or multi-part construction facilitates manufacture of the unit, as the upper portion may be removed, and the interior components such as the spectrometer may then be more readily installed or assembled in the interior of the housing, etc.

In operation, the spectrometer assembly within body portion 6A/6B preferably is located in the palm of the user's hand, thus enabling the spectrometer assembly to be positioned close to the object under test, and preferably so that no optical fibers or the like that serve to couple light from the object under test to the spectrometer assembly will be bent or kinked by user of the instrument (the adverse affects, such as optical transmission changes, from bending or kinking optical fibers are described in greater detail in the Referenced Patent Documents). Extending from, and preferably integral with, body portion 6A/6B is neck portion 8 (in the illustrated embodiment, neck portion 8 is formed from the upper and lower portions 6A and 6B of the body portion, although the present invention is not necessarily limited to this construction. With neck portion 8 also consisting of upper and lower portions, the upper portion may be removed such as to facilitate assembly, such as positioning of fiber optics or light guiding members, etc., into the tip, etc. Preferably, the neck portion extends in a curved manner in a direction away from the body portion and toward the tip and the person whose tooth is to be measured (as more fully described elsewhere herein). As will be appreciated, the neck portion may extend in a direction and length so as to facilitate measurement of the target object, such as a tooth in a patient's mouth.

Extending from, and preferably integral with, neck portion 8 is tip portion 10. Optics, such as light guiding fiber optics or the like, preferably carry light to tip end 12 at end of tip portion 10, at which point the light leaves the instrument in order to illuminate the tooth or other object or material, and return the light to the spectrometer for analysis. With such a probe configuration, with neck portion 8 and tip portion 10 configured such as illustrated, the instrument may more readily extend into the mouth of a patient and serve to facilitate the measurement of teeth and the like. Preferably, neck portion 8 and tip portion 10 together may serve as a form of cheek retractor, or have a length and shape, so as to enable measurement of posterior or inside/back teeth of a patient, as opposed to other techniques in which only anterior or front teeth may be measured. While the illustrated shape of FIG. 1 is exemplary, what should be appreciated is that body portion 6A/6B may house the spectrometer/spectrometer, while neck portion 8 and tip portion 10 extend away from body portion 6A/6B and carry source and receiver fiber optics or light guides to end 12 of tip portion 10, with neck portion 8 and tip portion 10 collectively having a length and/or shape to facilitate the measurement of desired samples, such as teeth, which may be located in difficult to reach places (such as posterior teeth in the mouth of a patient).

In accordance with preferred embodiments, the neck portion is configured to have an upper portion that includes a location (such as location 4, as illustrated in FIG. 1) for placement of a user's index finger. This location may have an indented portion or other textured area or friction surface (such as small bumps, a rubber surface or the like that tends to increase the friction between the user's index finger and the instrument) such that a user's index finger may be securably be positioned at that location. With the user's index finger reliably positioned at such a location on the neck portion, the tip portion of the instrument may be more precisely moved towards a desired or predetermined location on the tooth or other object so that the tip may measure the desired or predetermined location.

Also in accordance with preferred embodiments, one or a plurality of switches are provided for activation and/or control of the instrument, preferably located and operated in a manner such that the measurement is not adversely affected by undesired movement induced by the switch activation. One or more switches may be located on a lower surface of the body portion such that the switch may be activated by a squeezing motion of one or more of the user's fingers, while not pulling the instrument away from the desired or predetermined location on the tooth or other object. In addition (or alternatively), the tip may move respect to other parts of the tip portion or the neck and body portion such that the movement of the tip may be detected electrically, mechanically or optically. In one exemplary preferred embodiment, a membrane or spring activated-type switch is positioned within location 4, such that a movement of the user's index finger causes activation of the switch, which may be detected such as to initiate a measurement (which may be a measurement of the object under test, a calibration or normalization reference or standard, etc.). What is important is that body portion 6A/6B include an intuitive and nature placement for position of one or more of the operator's fingers, preferably in a manner that naturally and intuitively guides the probe tip towards a desired area for measurement, with a switch that may be activated with a slight and natural movement that does not tend to cause undesired motion of the probe tip from the desired area for measurement (as described in the Referenced Patent Documents, for example, movement away from such a desired area or at an undesired angle, etc., may be detected or quantified, with optical measurements either adjusted or rejected based on the movement or amount of movement, etc.).

Figure 2:
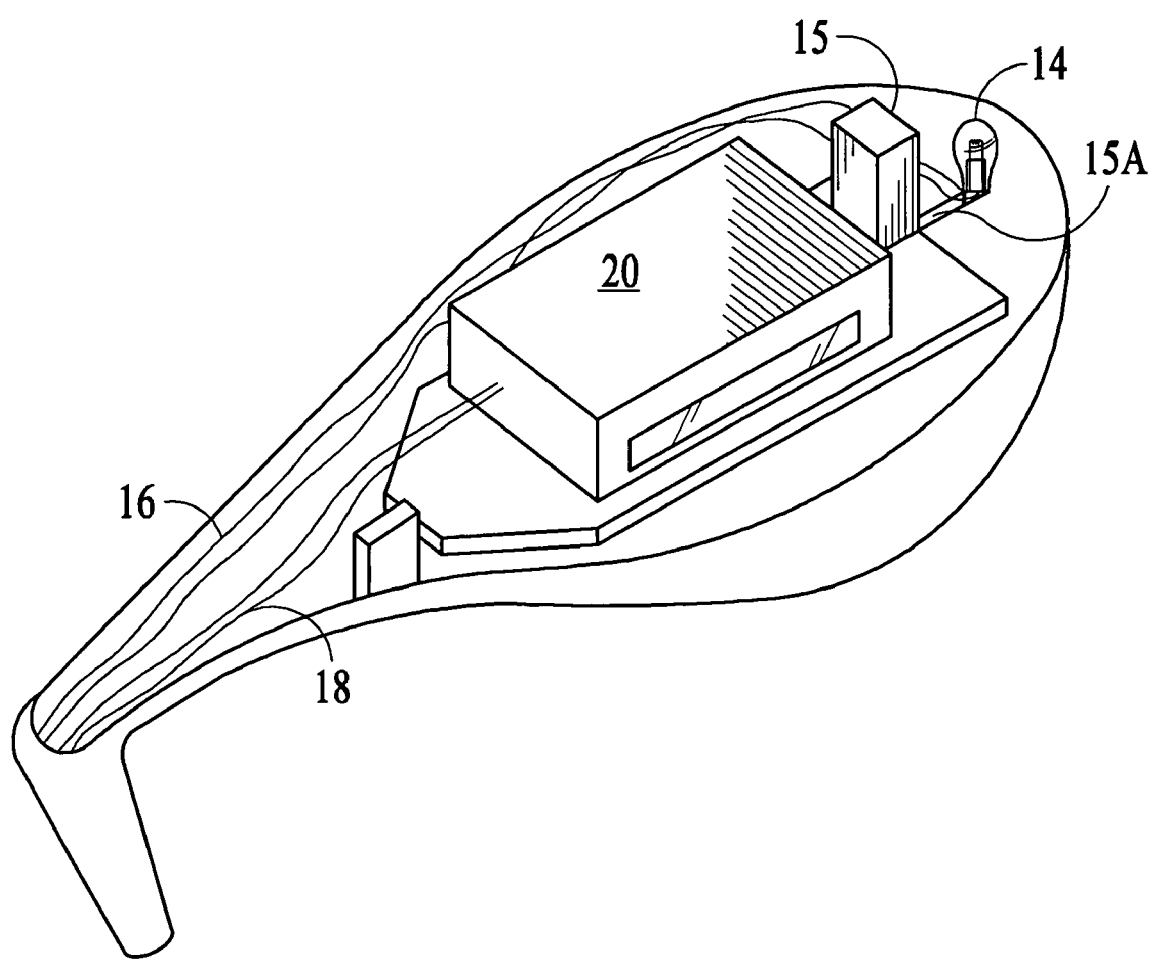
FIG. 2 is an interior view of a spectrometer/spectrophotometer housing arrangement in accordance with an exemplary preferred embodiment of the present invention.

FIG. 2 is an interior view of a spectrometer/spectrophotometer housing arrangement in accordance with an exemplary preferred embodiment of the present invention. FIG. 2 illustrates in greater detail general aspects of such an exemplary preferred embodiment, which other figures will illustrate preferred optical and spectrometer configurations, etc., that may be used with such exemplary arrangements as are illustrated in FIG. 2.

Generally, implementations of such embodiments constitute spectrophotometers, which generally consist of a light source (e.g., light source 14) that provides light to the object under test (e.g., such as via light source member 16, which may constitute a fiber optic or fiber optic assembly). Light is returned from the object and received and carried (e.g., such as via light receiver member 18, which may constitute a fiber optic or fiber optic assembly or multiple fiber optics, as in preferred embodiments to be described hereinafter) to spectrometer assembly 20 for analysis. In accordance with preferred embodiments of the present invention, however, spectrometer 20 is positioned inside of body portion 6A/6B so that the bulk of spectrometer assembly 20 is effectively positioned inside the operator's hand, with neck portion 8 and tip portion 10 extending away from body portion 6A/6B in a manner to facilitate measurement of objects such as teeth, which may be inconveniently located, such as inside of a person's mouth.

As will be appreciated from FIG. 2, light source 14 may be located within or integral with body portion 6A/6B, and a suitable power source (such as battery 15 via power conductors 15A) may provide power for light source 14 and the electronics of spectrometer assembly 20. In such embodiments, the underside of body portion 6A/6B may carry a display device (such as generally illustrated by display device 6C in FIG. 1) that outputs data indicative of the optical characteristics of the object being measured (such as, as discussed in detail in the Referenced Patent Documents). This may be, for example, an output of a closest color or shade match (or closest match), such as a Pantone or Vita shade guide value, a paint or other pigment specifier or formulation, pass/fail indication, etc. Also as will be appreciated, spectrometer 20 may include a processing device (again, such as discussed in detail in the Referenced Patent Documents), which may include memory, input/output circuitry and the like, such that data generated by spectrometer assembly 20 may not only be used for color or shade prediction, but be displayed or transferred to another computer device as spectral or other data. Such data transfer from the handheld device may be by customer or standard serial or parallel interface, USB, etc., or may be wireless, such as using a wireless transceiver arrangement such as based on what are known as the Bluetooth or 802.11 or other wireless protocol, or may be a docking station-type data transmission (i.e., data is collected and locally stored within spectrometer assembly 20 or elsewhere within body portion 6A/6B, and subsequently transmitted via a wired or wireless connection by positioning body portion 6A/6B within a docking station or cradle, with electrical connectors for data transmission or battery recharging, etc., on body portion 6A/6B mating with corresponding electrical connectors on the docking station or cradle, etc.). What is important is that the handheld device include one or multiple spectrometers such as illustrated by spectrometer assembly 20, which spectrally analyze light returned from the object under test, with the data generated by the spectral analysis further processed, either with processing circuitry within spectrometer assembly 20 (or elsewhere within or integral to body portion 6A/6B, etc.) or external thereto, such as by a wired or wireless data connection to an external computer/processing device, which may further process the data, such as for shade or color or pigment prediction, display or color or spectral data, data storage, transmission to remote locations for processing or display or for production of articles based on data generated by spectrometer assembly 20, etc. Such exemplary uses of data generated by spectrometer assembly 20 are discussed in greater detail in the Referenced Patent Documents.

In a similar manner, the light provided to the object under may be generated by a light source integral to body portion 6A/6B (such as via light source 14), or may be generated by a light that is not integral to body portion 6A/6B but is instead generated external to body portion 6A/6B and provided to body portion 6A/6B via an optical cable (such as a light source fiber optic). In one such embodiment, an external unit provides light to body portion 6A/6B via a fiber optic cable or cable assembly (e.g., collection of fiber optics), with data and/or power cables being provided along with the fiber optic cable/cable assembly from the external unit. With such embodiments, the external unit may include a power supply, light source, display and associated electronics/processing, such that body portion 6A/6B includes fiber optics to provide light to and from the object under test, with spectrometer assembly 20 generating spectral data, which may then be transferred to a processor in the external unit via the data cables. As will be appreciated, the light source optic cable/cable assembly and the data and/or power cables may be provided, for example, in a single monocoil, such as may be constructed with stainless steel, aluminum or other material known in the art. Such exemplary arrangements will be explained in greater detail hereinafter.

Figure 3:
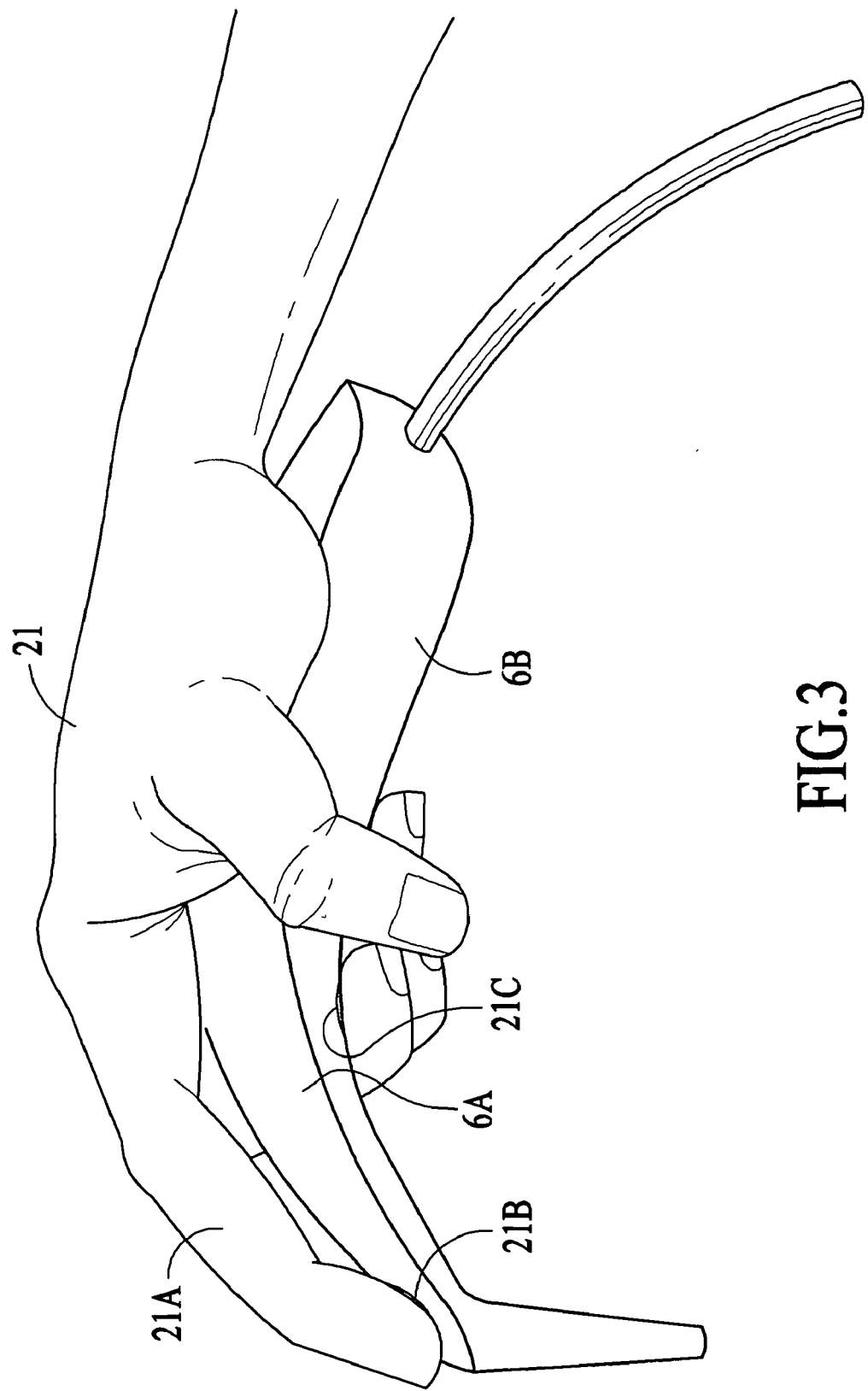
FIG. 3 is an illustration of a user utilizing a spectrometer/spectrophotometer arrangement in accordance with an exemplary preferred embodiment of the present invention.

FIG. 3 is an illustration of a user utilizing a spectrometer/spectrophotometer arrangement in accordance with an exemplary preferred embodiment of the present invention. As illustrated in FIG. 3, hand 21 of a user or operator may grasp body portion 6A/6B such as by wrapping of fingers around body portion 6A/6B, preferably with index (or other) finger 21A being positioned in an extended or semi-extended manner (such as is illustrated) with finger tip 21B being positioned within or on a physical placement feature on neck portion 8 (see, e.g., location 4 discussed in connection with FIG. 1). A switch for initiation of a measurement, for example, may be located under finger tip 21B or under finger tip(s) 21C (such as previously described).

What is important to note from FIG. 3 is that spectrometer assembly 20, within body portion 6A/6B is positioned generally within the volume created by hand 21 holding body portion 6A/6B, preferably with a natural and physically intuitive position for the index and other fingers of the user/operator, and preferably with a suitable membrane, spring or other switch located and configured in a manner that it may be activated by the user/operator without a significant tendency to cause movement of the tip end from the desired area for measurement on the object under test. Further, in embodiments where body portion 6A/6B is coupled to an external unit via an optical and/or electrical cable or cable assembly (such as described elsewhere herein), as illustrated in FIG. 3 cable/cable assembly 22 is positioned to exit body portion 6A/6B preferably from a rear portion of body portion 6A/6B, which tends to cause cable/cable assembly 22 to be below the arm of the user/operator as illustrated. With other instruments, a cable often times exits a probe or handpiece assembly so as to over the user's arm and/or hand and tend to pull down the user's arm and/or hand. In accordance with embodiments of the present invention, however, it has been determined that desirable spectral/optical measurements may be made with a spectrometer positioned within a handpiece as described and illustrated, with any cable/cable assembly extending from the handpiece exiting the body of the handpiece at a position to be below the arm/hand of the user, such that the weight of any such cable/cable assembly does not tend to pull the hand or arm of the user during operation, or to cause forces that would cause the user to tire more easily from use of the instrument, etc. This has been determined to be particularly true when the present invention is applied to fields such as dentistry, when a dental professional may desire to carefully target the probe tip to one or more desired areas of a tooth or teeth (such as for measuring a plurality of anterior and posterior teeth, as described elsewhere herein), with the handpiece being configured to enable the dental professional to guide the probe tip to the desired area or areas, with a switch configured to initiate measurements in a manner not to cause movement of the handpiece tip from the desired area or areas, and without any cable/cable assembly tending to pull the dental professional's arm or hand in a manner that may likewise tend to cause movement of the handpiece tip from the desired area or areas, etc. Of course, as described elsewhere herein, a cable/cable assembly extending from the handpiece is optional, and in other embodiments wireless data transmission, docling station data transmission, etc., may be utilized (and in such embodiments there may be no cable/cable assembly extending from the handpiece, etc.).

As described elsewhere herein and in the Referenced Patent Documents, in preferred embodiments spectral measurements are made with a highly miniaturized spectrometer assembly, which preferably consist of an array or other plurality of sensors (preferably consisting of light to frequency converters), with light coupled to at least certain of the sensors via filters or filter elements (which preferably are interference filters, and which may be discrete bandpass type filters, or which collectively may consist of a color gradient or linear variable type filter, etc.). Preferably, light is coupled from a light source to the object under test via one or more light sources, which may be fiber optics, and preferably light is received from the object under test and coupled to the sensors via the filters or filter elements. Embodiments of the present invention provide improvements and enhancements to concepts such as the foregoing, and enable improved systems and methods for measuring the optical properties of optically complex materials, including objects that are translucent, pearlescent, etc., and including objects such as teeth, dental restorations, gems, etc. In certain preferred embodiments, a multi-spectrometer design is utilized to provide multiple spectral-type measurements, preferably in parallel, and preferably with different source-receiver combinations that enable various complex materials to be optically measured.

Figure 4:
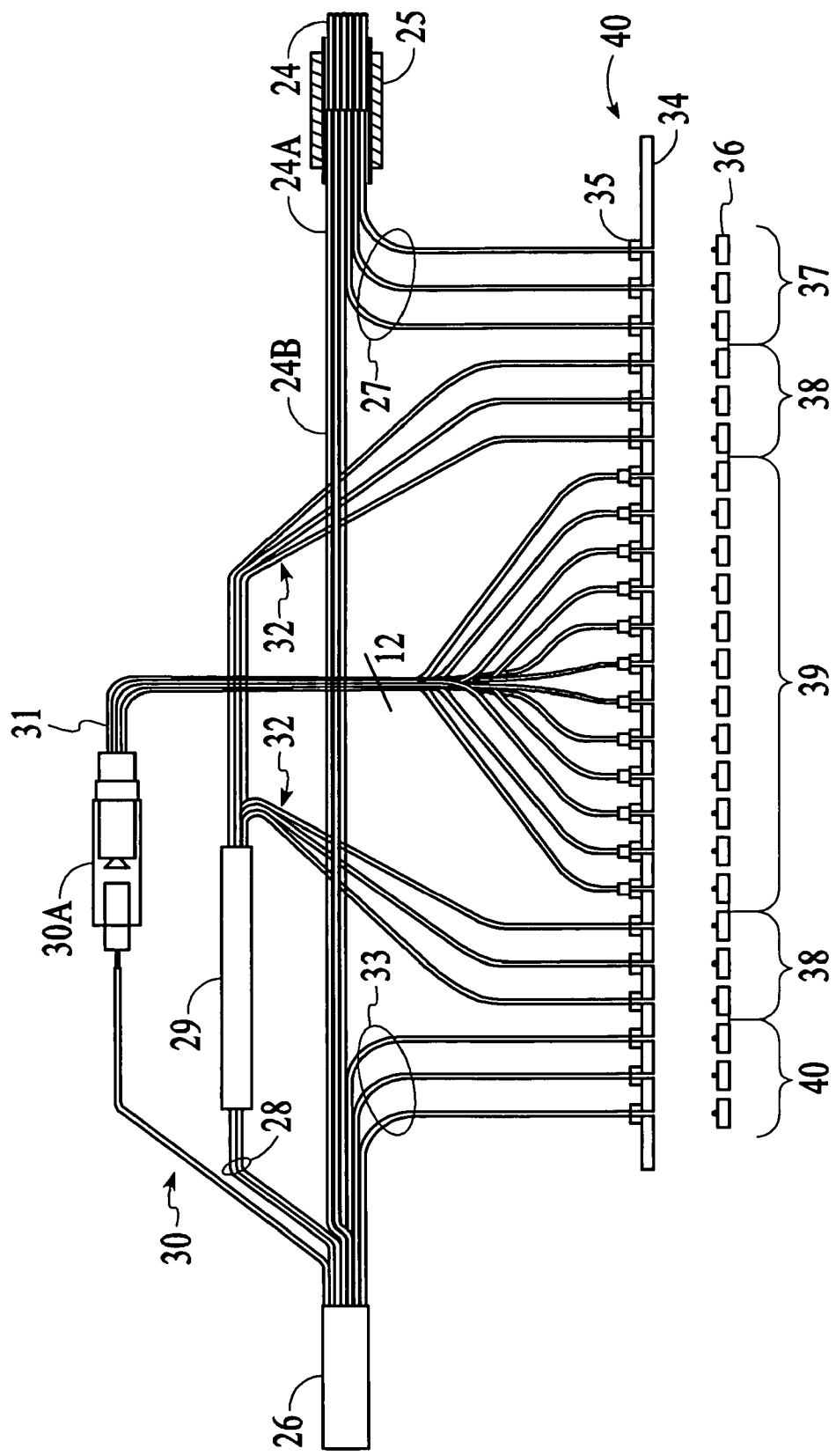
FIGS. 4, 5A-5D and 6 illustrate exemplary probe, optical and spectrometer configuration for an exemplary preferred multi-spectrometer embodiment of the present invention.

Referring now to FIG. 4, an exemplary embodiment of such a multi-spectrometer design will now be described. Light from a light source (not shown in FIG. 4; preferably an incandescent lamp with generally known optical properties, such as color temperature) is provided via optical fiber 24 (e.g., which may be a 4.0 millimeter glass or other optical fiber bundle). Light from fiber 24 is coupled to fiber bundle 24A, three fibers of which (i.e., fibers 27, which may be 1.0 millimeter plastic fibers) are coupled to three sensors via filters (preferably three separate bands of predetermined wavelengths over the visible band; e.g., bandpass interference filters). Fibers 27 and the associated filters will be understood to constitute a first spectrometer or spectral measuring device, which preferably serve to track and monitor the output of the light source. As will be understood, the choice of three fibers and three bands to track the light source is exemplary; one, two, three, four or more bands could be similarly be used to track the light source, but three bands, along with some understanding of the properties of the light source, have been determined to provide a sufficient level of information regarding the light output of the lamp; as will be further understood, in the event of lamp drift, such may be detected and the sensed via fibers 27, and spectral measurements of the object under test either adjusted or rejected due to changes in the light source output, etc. In FIG. 4, elements 35 generally illustrate a ferrule coupled to the individual fibers, which may be utilized to couple the fiber to aperture plate 34, which serves to position the end of the fiber so as to couple light to filters/sensors 36 (in FIG. 4, the filters and sensors are shown as a combined item for discussion purposes; it is understood, based on the description elsewhere herein and in the Referenced Patent Documents, that the particular coupling details between the fiber ends and the sensors may be configured in a variety of ways and may include, for example, aperture plates, lenses, lens assemblies, spacers, etc.; what is important for this particular embodiment is that light from the lamp is coupled to sensors via filters in order to provide a lamp monitoring spectral sensing implement which monitors the lamp source output, etc.). Filters/sensors/electronics 40 of FIG. 4 generally refers to the filters and sensors, and associated electronics for reading the outputs of the individual sensors, for implementing multiple spectrometers and topology angle sensors, more details of which may be understood from the Referenced Patent Documents.

Figure 6:
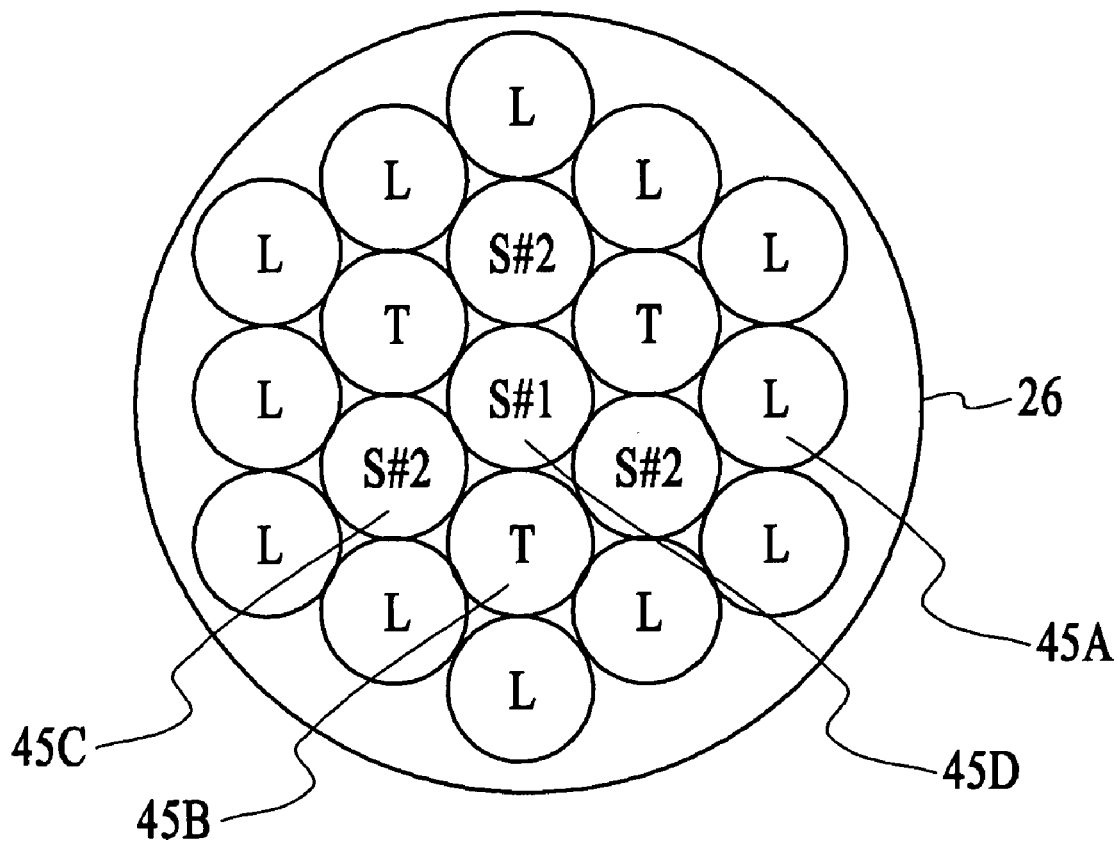

Fibers 24B from fiber bundle 24A are provided to probe tip 26 as illustrated. In the illustrated embodiment, fibers 24B constitute 12 fibers, which may consist of 1.0 millimeter plastic fibers. The arrangement of fibers 24B in probe tip 26, which serve to provide a plurality of light sources, or effectively a ring of light, are illustrated in FIG. 6 and will be described in greater detail hereinafter.

Light returned from the object under test is received by probe tip 26 via a plurality of light receivers. Such light receivers preferably may consist of a center light receiver 30, preferably a 1 millimeter plastic fiber, and also a first set (preferably three) of light receivers 33 not from the center of the probe tip and a second set (preferably three) of light receivers 28 also not from the center of the probe tip.

Center light receiver 30 is preferably coupled to a plurality of sensors via a plurality of filters, with the filters preferably providing bandpass filters spaced over the spectral band(s) of interference; for example, the filters may have bandpass characteristics such that the filters collectively span the visible band, such as described in the Referenced Patent Documents. In a preferred embodiment, center light receiver 30 is coupled to randomized fiber optic 31, which preferably has and input that receives light via light receiver 30 via optical coupler/splitter 30A (which may include a lens to collimate light from light receiver 30 to more optimally couple the light provided to randomized fiber optic 31), and has twelve outputs, each of which provides light that is coupled to a sensor through one of the filters. As described in the Referenced Patent Documents, the use of a such a randomized implement may help serve to destroy any angular or similar dependencies of the light received by light receiver 30, with the light provided to the twelve outputs being more or less equal or having reduced dependency as to where on light receiver 30 is the received light receiver (and at what angle, etc.) over the twelve outputs. Preferably, randomized fiber optic 31 is an optical implement which constitutes a large number of preferably glass fibers, with an input area that is randomly divided and apportioned to N preferably 12) output areas, which in the illustrated embodiment constitute 12 fiber optic bundles each of which couples light to a sensor via a filter. As also described in the Referenced Patent Documents, such a randomized implement efficiently provides light to the filter/sensor combinations with less angular dependencies, etc. The N preferably 12) outputs of randomized fiber optic 31, and the associated filter/sensors, preferably provide a first spectrometer/spectral sensing implement for generating spectral data based on the light received from the object under test.

Light receivers 28 preferably are coupled to sensors via filters in order to provide a second spectrometer/spectral sensing implement for generating spectral data based on the light received from the object under test. In the illustrated embodiment, light receivers 28 constitute three fiber optics. While three fiber optics may be coupled to filters/sensors and provide a three band spectral sensing device, in the illustrated embodiment six spectral bands are utilized for the second spectrometer/spectral sensing device. In the illustrated embodiment, the three fibers of light receivers 28 are coupled to light pipe 29 (which may be a 2 millimeter plastic light pipe), which serves to couple and mix and diffuse light from (preferably) three input fibers 28 to (preferably) six output fibers 32. The preferably six output fibers are coupled to filters/sensors as illustrated. The preferably 6 output fibers, and the associated filter/sensors, preferably provide a second spectrometer/spectral sensing implement for generating spectral data based on the light received from the object under test.

Light receivers 33 typically are coupled to sensors via neutral density filters (or no filters) and are preferably used to provide topology sensors (see, e.g., the discussion in the Referenced Patent Documents). In yet other alternative embodiments, light receivers 33 could be provided to sensors without filters, could be provided to sensors via fine bandpass filters and look at only particular spectral lines (for example, in order to detect the presence of specific materials that reflect or emit light in such particular spectral bands, etc.). In preferred embodiments, however, such light receivers 33 serve to provide positional or topology information (e.g., angle of the probe with respect to the surface of the object under test), such as described in the Referenced Patent Documents.

FIGS. 5A-5D illustrate exemplary routing and mapping of fibers in such embodiments. As will be understood from FIGS. 5A-5D, the sensors and filters and fiber optic inputs to the assembly 40 are in two rows; as FIGS. 5A-5D provide only a top view, only the top row is shown. In the illustrated embodiment, a bottom row also exists, and thus 24 total sensors are provided in the illustrated embodiment. Of course, as will be understood to those of skill in the art, the particular number of filters and sensors may be readily adapted to the particular application, and the present invention is not limited to the particular numbers in the illustrated embodiments.

Figure 5B:
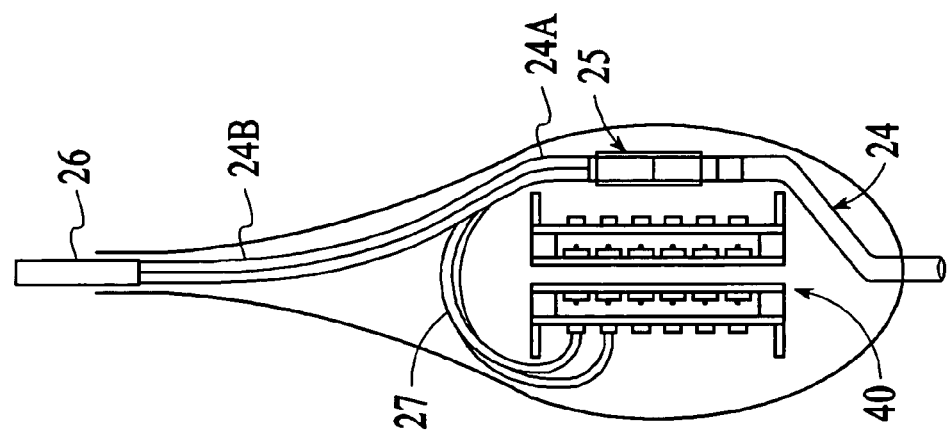
Figure 5A:
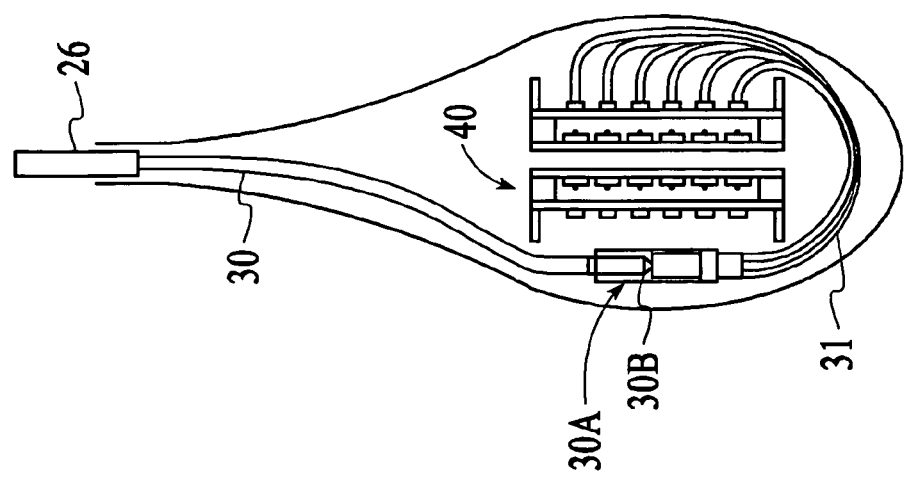

In FIG. 5A, center light receiver 30 extends from probe tip 26 to coupler 30A, which preferably includes lens 30B, which serves to collect and collimate light from light receiver 30 and couple the light to the input area of randomized fiber optic 31, which serves to randomize and split the light into separate outputs, as previously described. The outputs of the randomized fiber optic 31 are coupled to filters/sensors/electronics 40 to provide a first spectrometer/spectral sensing implement, as previously described.

In FIG. 5B, light source fiber bundle 24 is coupled to coupler 25. Fibers 27 of fiber bundle 24A are coupled to filters/sensors/electronics 40 for purposes of monitoring and tracking the light source, as previously described. Fibers of fiber bundle 24B are provided to probe tip 26 and provide a plurality of light sources, also as previously described.

Figure 5D:
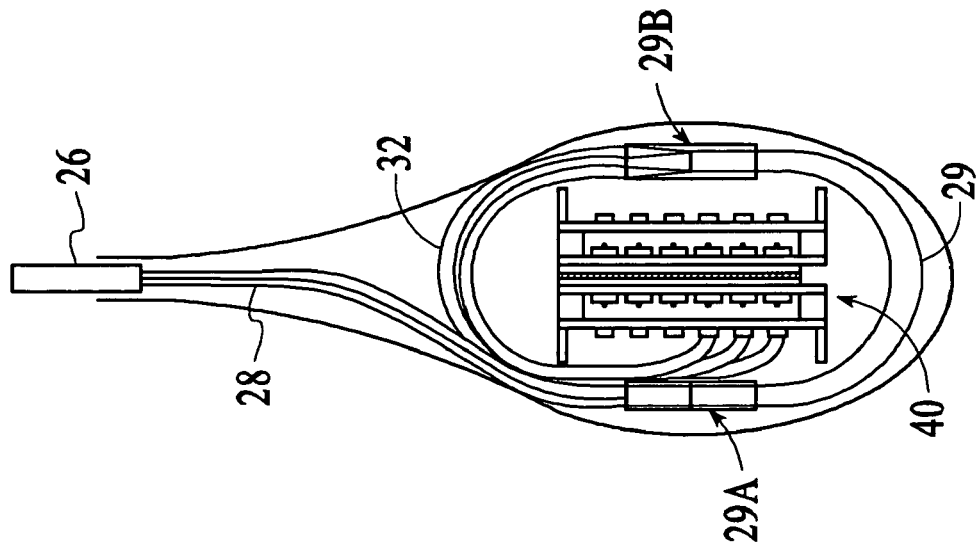
Figure 5C:
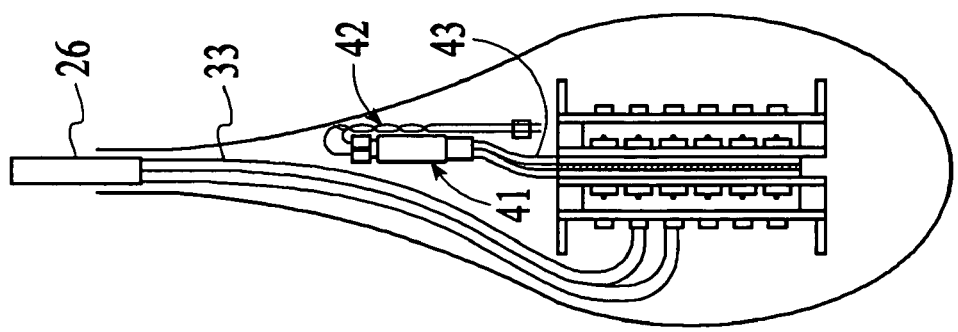

In FIG. 5C, light receivers 33, which preferably are inner ring fibers (see FIG. 6), extend from probe tip 26 and are coupled to filters/sensors/electronics 40 for purposes of, for example, providing topology or angle sensors, such as previously described. Also illustrated in FIG. 5C are bias lamp 41, power wires 42 and light conductor 43. As described in greater detail in the Referenced Patent Documents, in preferred embodiments bias light is provided to the sensors, which guarantee a minimal amount of light to the sensors (as will be understood from the Referenced Patent Documents, light from bias lamp 41 is not light that is provided to and returned from the object under test, but instead is a preferably separate light source that serves to bias the light sensors). Under power provided by wires 42 (with the power preferably obtained from the power supply providing power to the sensors, for example), bias lamp 41 generates bias light, which is controllably conducted to the sensors via light conductor 43.

In FIG. 5D, light receivers 28, which also are preferably inner ring fibers (see FIG. 6), extend from probe tip 26 and are coupled to light pipe or coupler 29, which serves to couple/mix/diffuse light from light receivers 28 to fibers 32. The outputs of the fibers 32 are coupled to filters/sensors/electronics 40 to provide a second spectrometer/spectral sensing implement, as previously described.

FIG. 6 illustrates an exemplary end view of probe tip 26. Center light receiver 45D is positioned generally at the center of probe tip 26. As will be understood, center light receiver generally may be considered the end of light receiver (fiber) 30, which is coupled to a first spectrometer/spectral sensing implement. A first ring is provided around center light receiver 45. In the first ring are arranged light receivers 45C and 45B, which generally may be considered the ends of light receivers 28 and 33, respectively. Light receivers 45C preferably 3) provide light that is ultimately coupled to a second spectrometer/spectral sensing implement. Light receivers 45B preferably 3) provide light that is coupled to sensors such as for purposes of sensing topology or angle. A plurality of light sources 45A preferably are provided in a circular arrangement in probe tip 26 (12 being illustrated in this exemplary embodiment). The plurality of light sources 45A generally constitute the ends of the fibers of fiber bundle 24B, as will be understood from the description elsewhere herein. The plurality of light sources 45A generally constitute a ring light source in probe tip 26.

Based on the foregoing, it will be understood that an instrument may be provided that utilizes multiple spectrometers in parallel, including multiple spectrometers that may serve to make spectral measurements, preferably in parallel, of the object under test. As described in greater detail in the Referenced Patent Documents, the numerical aperture, diameters and spacing of the light sources and receivers define a "critical height" below which light that is reflected from the surface of the object under test cannot be received and propagated by the light receivers. Measurements below the critical height thus are generally not dependent upon surface characteristics, as light reflected from the surface is not going to be received by the light receivers and thus sensed by the spectrometers. Light that enters the light receivers generally is light that enters the bulk of the material of the object, is scattered and displaced so that it can exit the material at a position and angle to be received and propagated by the light receivers (see the Referenced Patent Documents for a more detailed discussion of this phenomenon). Consider probe tip 26 being in contact with the surface of the object under test. In such a condition, the various source/receiver combinations provided by probe tip 26 each will be below the critical height. While conventional approaches tend to characterize optical properties that include surface reflected light (and thus tend to be more sensitive to surface irregularities, angle, etc.), it has been discovered that optically more complex objects such as teeth, which are highly translucent, may be more optimally quantified with such below the critical height measurements. With the multi-spectrometer approach of the present invention, multiple spectrometers may make multiple below the critical height measurements in parallel, and thus provide substantial optical data from which optical characteristics of the object under test (such as a shade or color prediction) may be determined.

Without being bound by theory, a discussion of certain benefits and principles of the foregoing approach will now be described. As will be appreciated from FIG. 6, center light receiver 45D is generally equi-distant from the various light sources 45A. Thus, light that is received by light receiver 45D generally is light from light sources 45A that enters the object under test, penetrates some optical depth, gets scattered, displaced, etc., and is ultimately received by light receiver 45D. Generally, however, the light originates from a light source that is in essence the same distance away from the light receiver (as will be appreciated from FIG. 6, light receiver 45D is not precisely the same distance from all of the light sources 45A, but generally are about the diameter of the fibers of the inner ring away from the lights sources 45A). Each of light receivers 45C, on the other hand, is a varying distance from the various light sources 45A (i.e., some are closer to the light sources and some are farther away from the light sources). Light receivers 45C, with its varying spacings from light sources 45A, collectively receive light that may be considered to be more of an "average depth" or optical path length within the material of the object under test (again, some close and some far away). Again, without being bound by theory, it has been determined that light receivers 45C may be used to make spectral measurements that less sensitive to the thickness of the material under test, as compared to the center light receiver 45D, which has been observed to be more sensitive to thickness. In the case of materials such as teeth or dental restorations, the perceived optical characteristics may be a function of various layers constituting the materials. In attempting to characterize such complex optical materials, it has been determined that using multiple spectrometers to make multiple measurements, with varying spacings between the sources and receivers, varying average optical path lengths or effective optical depths of the measurements, etc., provide a much greater amount of information from which to make, for example, shade or color predictions.

For example, for an instrument that is used to shade match teeth or dental restorations, the material may be a tooth or a ceramic restoration. The constituent materials generally have different optical properties, and may have different layers of differing thicknesses of differing materials in order to produce colors that are perceived to be the same by viewing human observer. Having only a single spectral measurement, for example, has been determined to provide less than sufficient data for a sufficient shade or color determination or prediction.

In accordance with the present invention, the multiple spectrometers each make spectral measurements. Depending upon the type of material under examination, for example a natural tooth versus a dental restoration (and for example a denture tooth versus a porcelain-fused-to metal "PFM" crown), with the present invention different shade prediction criteria may be utilized. For example, user input may inform the instrument what type of material is under examination; alternatively, the instrument could collect data from the multiple spectrometers and predict the type of material (which could be confirmed or over-ridden by user input, etc.). In any event, after collecting spectral data, the instrument then desires to output a color or shade value. Typically, data is stored within the instrument in the form of lookup tables or the like, and measured data is compared in some form with the stored data of the various shades in order to predict and output the closest shade or color (see, e.g., the Referenced Patent Documents). In accordance with embodiments of the present invention, however, the measured data and lookup tables, or possible combinations thereof, may be more optimally utilized depending upon the type of material under test.

For example, if a natural tooth is under examination, spectral data may be collected from the first and second spectrometers. Data from the first (center receiver) spectrometer, which generally is more sensitive to thickness, may be used exclusively for shade or color prediction, or weighted more heavily in the shade prediction as compared to data from the second (ring receiver) spectrometer, which generally is less sensitive to thickness. For a PFM restoration, which could consist of thin layers (as compared to a comparable sized natural tooth), thickness dependencies could present much greater problems with attempting to perform shade matching or color prediction for PFM samples. If a PFM restoration is under examination, spectral data may be collected from the first and second spectrometers. Data from the second (ring receiver) spectrometer, which generally is less sensitive to thickness, may be used exclusively for shade or color prediction, or weighted more heavily in the shade prediction as compared to data from the first (center receiver) spectrometer, which generally is more sensitive to thickness.

As will be understood from the foregoing, depending upon the type of material under test, a different shade matching/prediction method or algorithm will be performed. In accordance with such embodiments of the present invention, a first type of material under test (e.g., a natural tooth) would utilize a first shade matching algorithm (e.g., weigh data from the first spectrometer more heavily than data from the second spectrometer), and a second type of material under test (e.g., a PFM restoration) would utilize a second shade matching algorithm (e.g., weigh data from the second spectrometer more heavily than data from the first spectrometer). In addition, depending upon the type of material under test, different optical parameters could be utilized, again with different weights. For example, a prediction based on the closest "delta E" match between the stored shades or colors may be used for a first type of material under test, while a prediction that gives more (or less) weight to, for example "delta L" or "delta c" or "delta h," may be used for second type of material (it being understood by those of skill in the art that L, c and h refer to luminance, chroma and hue of the well-know L-C-H system for representing color). Moreover, a first combination of data from the first and second spectrometers (with first weights given to the first and second spectrometers) and a first set of parameters (e.g., delta E) may be utilized for shade or color prediction for a first type of material, while a second combination of data from the first and second spectrometers (with second weights given to the first and second spectrometers) and a second set of parameters (e.g., delta L and/or delta c and/or delta h) may be utilized for shade or color prediction for a second type of material. With the present invention, multiple spectrometers, and/or multiple shade/color prediction/matching algorithms based on data from multiple spectrometers, may be utilized depending on the type of material being measured in order to more accurately predict/match shades and colors for a wide range of materials.

Other aspects of certain preferred embodiments of the present invention will now be described.

Referring now to FIGS. 7A-7D, an explanation will be provided of an improved barrier infection control implement that is preferably utilized in accordance with the present invention. As fields of application for the present include the dental and medical fields, and fields in which wet pigments or other materials could be applied (such as painting, printing), the probe used to make spectral or other optical measurements may come into contact with the object under test. In the case of dentistry, for example, contamination between patients is a serious concern. As explained in the Referenced Patent Documents, a barrier infection control implement may be utilized to present such contamination.

Figure 7A:
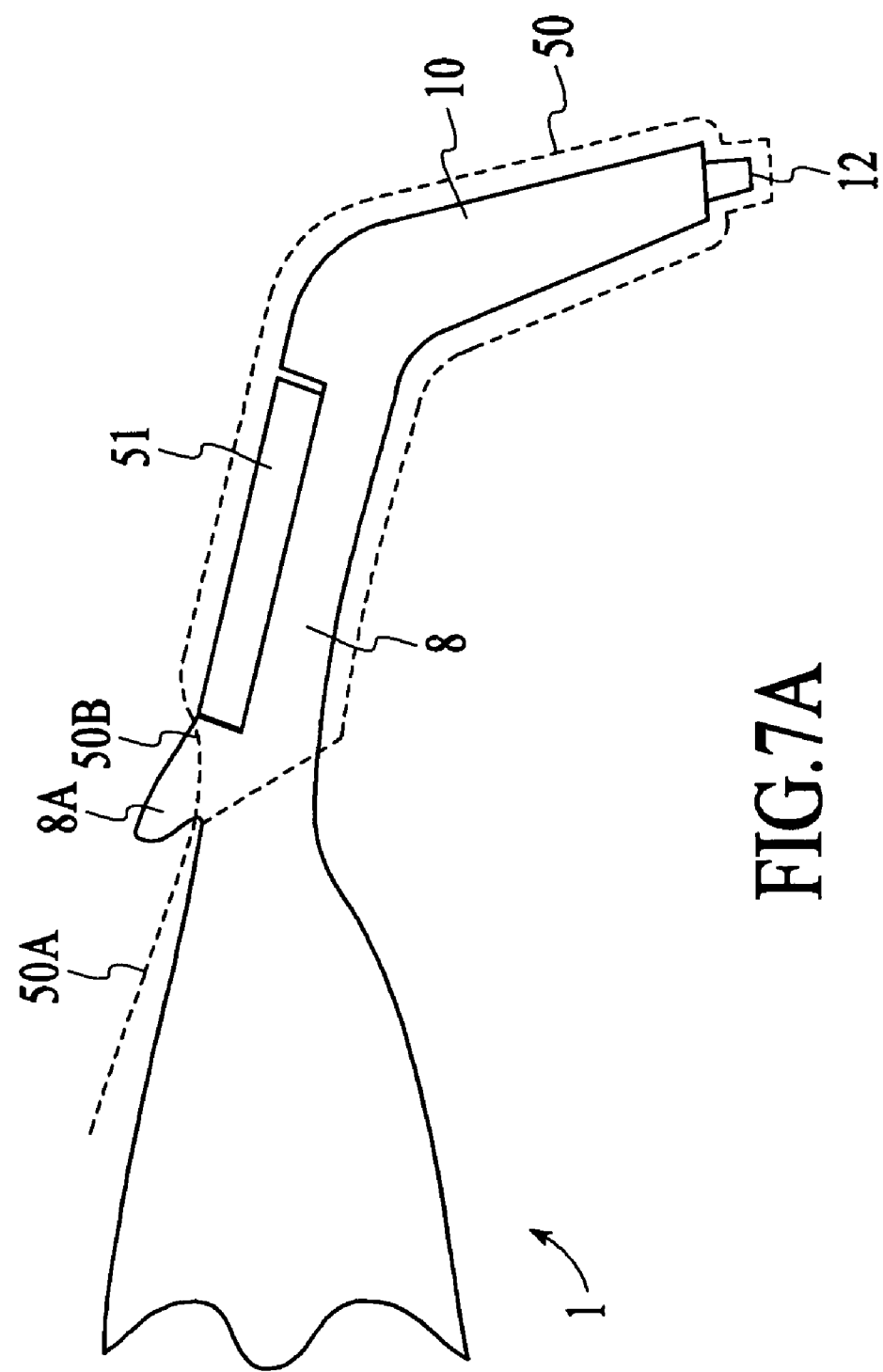
FIGS. 7A-7D illustrate an improved infection/contamination prevention implement (and its manufacture) utilized in certain preferred embodiments of the present invention.

In accordance with the present invention, as illustrated in FIG. 7A, a preferably pliant, stretchy, transparent barrier 50 fully encases and covers tip portion 10 of instrument 1. As illustrated, barrier 50 preferably is pulled up the length of tip portion 10 and over neck portion 8, preferably utilizing tab portion 50A, such that hole 50B slips over protrusion 8A. Protrusion 8A preferably is an implement that is added to neck portion 8 (either affixed to neck portion 8 or fabricated such as with a plastic molding process as an integral part of neck 8) such that a user may pull barrier 50 over the tip and neck portions such that hole 50B secures barrier 50 to the probe tip. The user preferably pulls the barrier into position tab portion 50A of barrier 50 (tab portion 50A preferably is integrally formed as a part of barrier 50, but which could be a separate material welded to the material of barrier 50). The act of pulling the stretchy material of barrier 50 such that hole 50B is over protrusion 8A also serves to pull the material of barrier to be closely conforming to end 12 of tip portion 10. In accordance with the present invention, optical measurements are made through barrier 50, and it is desirable that barrier 50 preferably provide a thin, wrinkle-free covering over end 12. As previously explained, in accordance with certain preferred embodiments, measurements are made "below the critical height." Thus, the material of barrier 50 is selected to have a thickness below (preferably much below) the lowest critical height of the various source/receiver combinations provided at end 12. It is further noted that the improved barrier described herein may desirably be utilized with the multi-spectrometer measurement technique described elsewhere herein, but such an improved barrier may also be utilized with the peaking measurement technique described in greater detail in the Referenced Patent Documents.

FIG. 7A also illustrates an improved switch/barrier control combination that is used in preferred embodiments of the present invention. As previously described elsewhere herein and in the Referenced Patent Documents, a user may initiate a calibration or measurement process by activation of a switch. An improved switch 51 is illustrated in FIG. 7A. Switch 51 preferably consists of an elongated bar, which may be a integral part of the switch, or may be a cap implement positioned over a switch type switch (with the spring providing an opposing force to the user's movement to activate the switch). The elongated bar of switch 51 may have ends on the distal and proximate ends (i.e., nearest to and farthest from end 12 of tip portion 10), which, for example, may fit into an indentation formed into neck portion 8. What is important is that the switch that the user activates to initiate a measurement have an elongated form factor, so that the switch extends a length down neck portion 8, so as to accommodate a variety of hand sizes. Thus, a user with a smaller hand size may just as easily activate switch 51 (by pressing on a lower portion of switch 51) as a user with a larger hand size (by pressing on a higher portion of switch 51). Also importantly, barrier 50, when in position on the instrument and secured thereon (such as by hole 50B over protrusion 8A), extends so as to completely cover switch 51. Thus, barrier 50 not only serves to prevent contamination, but also serves to provide a moisture or other contaminant barrier to switch 51.

Figure 7B:
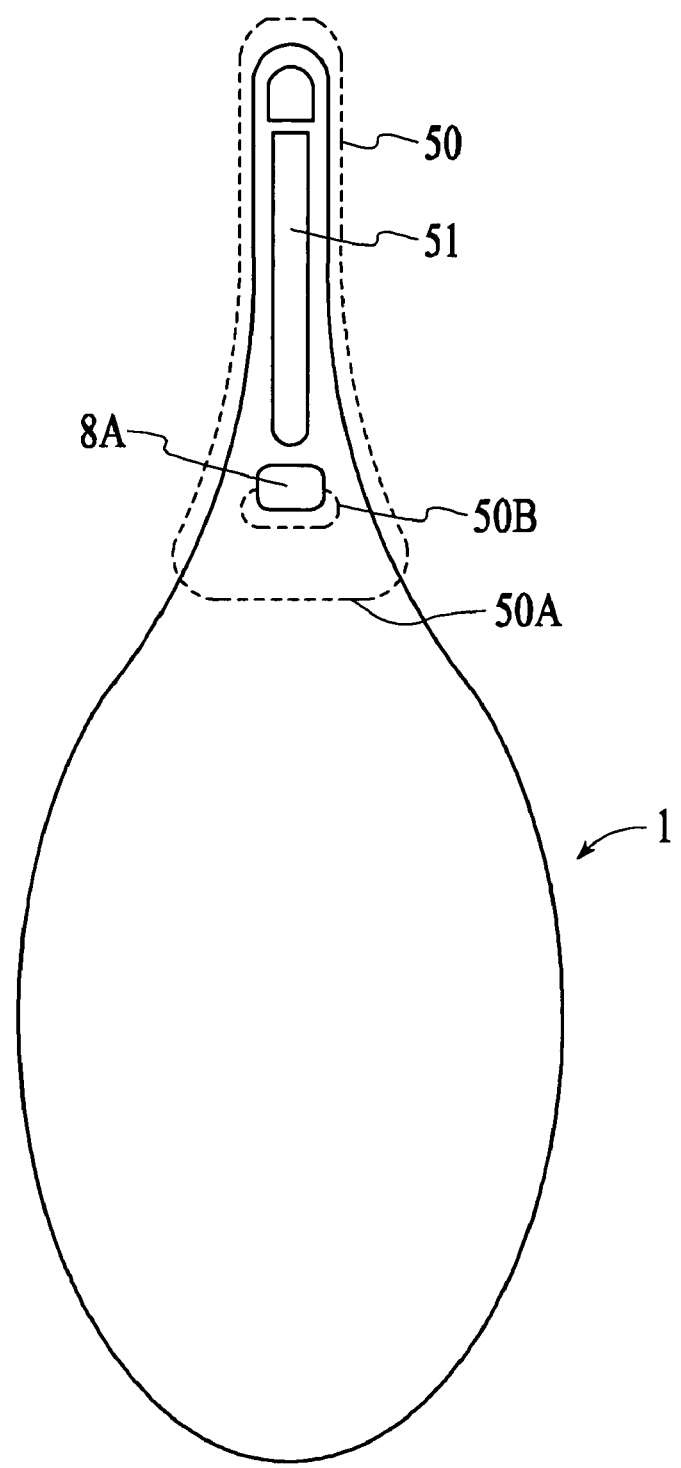

Referring now to FIG. 7B, another perspective of a preferred embodiment of barrier 50 and instrument 1 is provided. As illustrated, barrier 50 extends up and over tip portion 10 and neck portion 8 of instrument 1. As illustrated, hole 50B serves to secure barrier 50 by being positioned over protrusion 8A. Also as illustrated, elongated switch 51 is positioned under barrier 50, and will be activated through barrier 50 by depression of a user's (preferably) index finger.

Figure 7C:
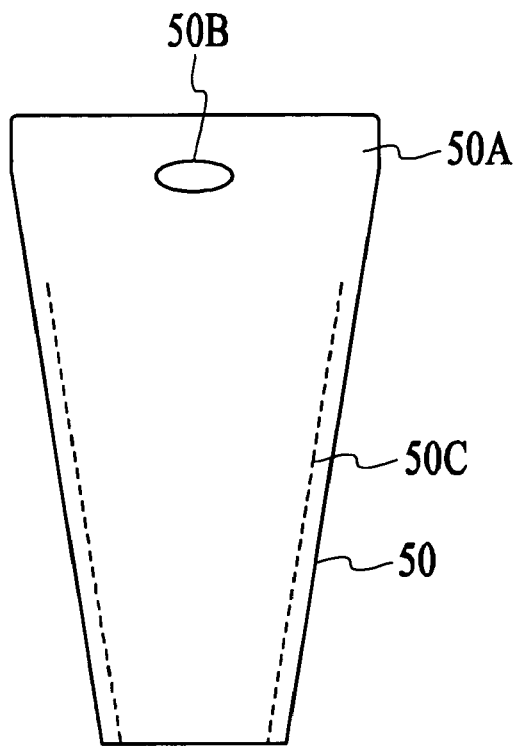
Figure 7D:
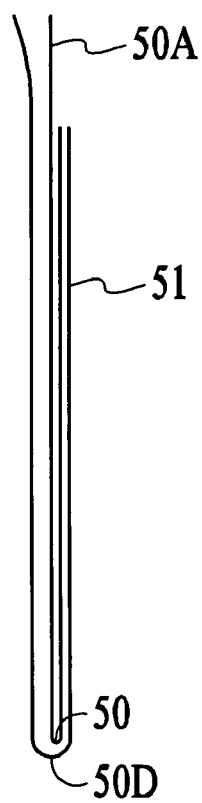

Referring now to FIGS. 7C and 7D, other perspectives of a preferred embodiment of barrier 50 is illustrated. While other constructions are within the scope of the present invention, barrier 50 preferably consists of a unitary material, which contains a suitable combination of properties such as strength, tear-resistance, transparency, pliability, stretchiness, etc. In a preferred embodiment, barrier 50 comprises polyurethane, but also may consist of a type of rubber, latex, or other material. Barrier 50 preferably is packaged with substrate 51 as illustrated in FIG. 7D. Substrate 51 may consist of paper or other suitable material that may protect barrier 50 prior to use, and may serve to facilitate application of barrier 50 to the instrument. Much like paper backing for a bandaid or similar instrument, the user may spread the opening of the pouch of barrier 50 by pulling the paper (desirably, the paper mildly adheres to barrier 50 during such application). As the pouch opens, the user inserts the probe tip into the pouch, and, with a combination of pulling the material of the barrier up and moving the probe tip down, the materials of the barrier stretches up and over the probe tip and neck, preferably so that hole 50B and protrusion 8A serve to secure the barrier onto the instrument. As a part of this operation, substrate 51 tears away from the material of barrier 50, and substrate 51 may then be disposed of. What is important is that the material of barrier 50 be provided to the user in a manner to secure its shape and to facilitate application to the instrument. As barrier 50 is desirably disposable, so desirably is substrate 51, which is disposed off after serving its purposes as described herein.

In preferred embodiments, an inner surface of the barrier 50 is relatively smooth or "satinized" in order to facilitate guiding the tip portion of the instrument into the barrier as described above, an outer surface of barrier 50 has a degree of tackiness or stickiness, particularly as compared to the inner surface, such that upon contact with the object under evaluation the tip portion mildly adheres to the surface of the object. With such an outer surface, measurement of objects such as teeth are facilitated, as the tip of the instrument may be directed to a desired spot of the object for evaluation, with the stickiness, or "non-slippery-ness," of the outer surface of barrier 50 serving to prevent movement of the tip from the desired spot on the object.

Preferably, barrier 50 is manufactured by cutting or otherwise forming the material to be of the desired shape, which may include punching or otherwise forming hole 50B. This preferably is performed on substrate 51, and thus the material of barrier 50 and substrate 51 desirably may be formed of the desired overall shape in a single step. Preferably, the size and shape of hole 50B corresponds to protrusion 8A in order to reliably secure barrier 50 onto the probe. The material of barrier 50, and preferably substrate 51, is then folded, preferably in an automated manner. It should be noted that the fold is asymmetric in order to form an extended tab portion 50A of barrier 50, which may be utilized to pull barrier 50 into proper position, such as previously described. In preferred embodiments, weld 50C is formed via an RF (or other radiant energy process) or thermal type process, and preferably through substrate 51. It should be noted that the weld of the material of barrier 50 does not extend the full length of the material, but extends so as to define an inner pouch of barrier 50, while providing a substantially complete seal in order to provide a suitable contamination/infection control implement. It also should be noted that end portion 50D of barrier 50 consists of a portion not having a seam across end 12 of tip portion 10. In this regard, the width of the material used to form barrier 50 has a suitable width such that, when welded to form the pouch, and when stretched into position, a relatively flat, wrinkle-free and seam-free covering is provided over end portion 12 of tip portion 10.

Other aspects of preferred embodiments of the present invention will now be described.

Figure 8:
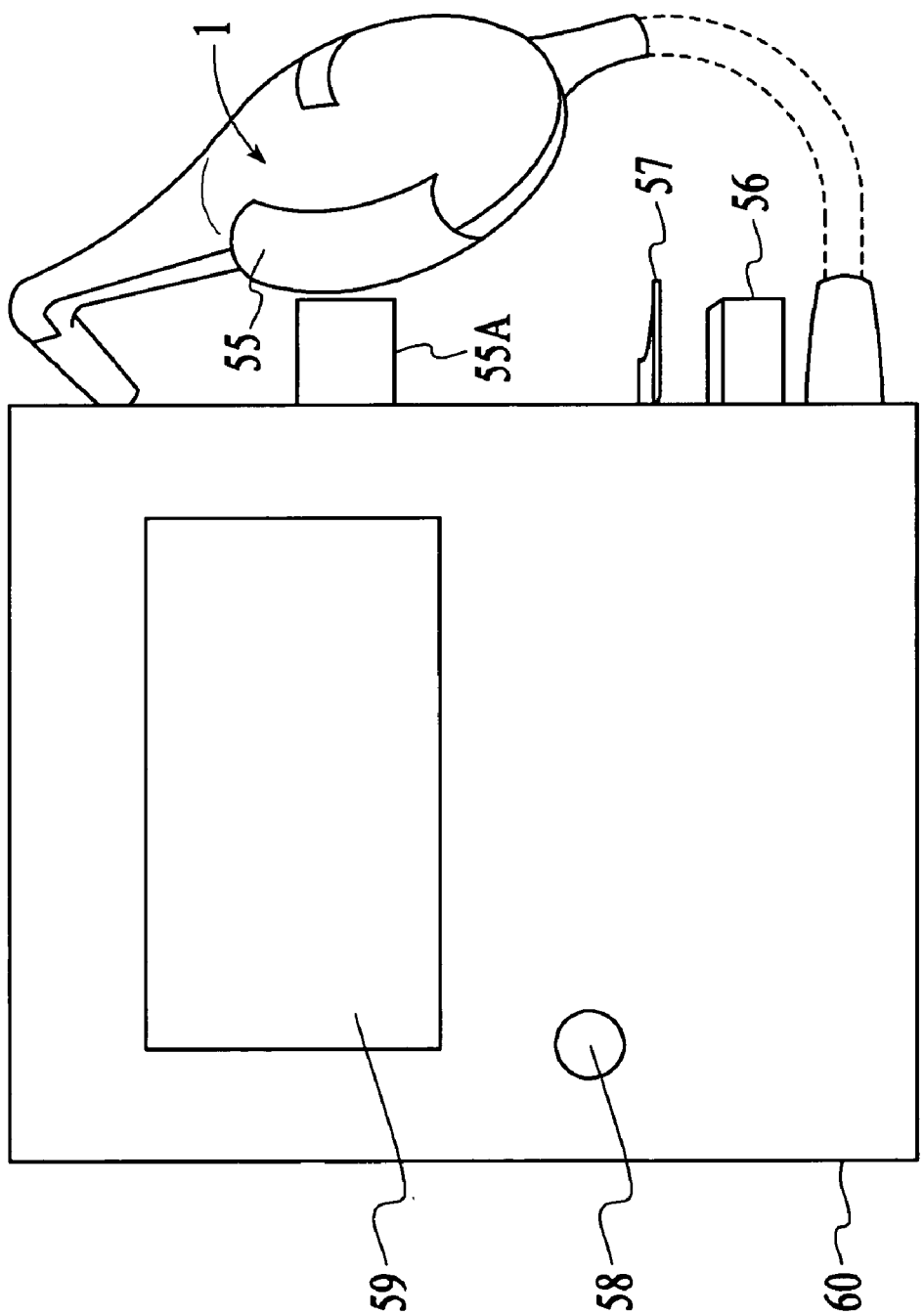
FIG. 8 illustrates an exemplary base unit and calibration block in accordance with an exemplary preferred embodiment of the present invention.

FIG. 8 provides an overview of an exemplary cabled implementation of a preferred embodiment of the present invention. Spectrometer/spectrophotometer or handpiece 1 (such as previously described) preferably rests in cradle 55 when not in operation. Cradle 55 preferably is secured to base unit 60 via arm 55A. On/off switch 58 preferably is utilized to turn on or off base unit 60, although in preferred embodiments, as a safety feature, base unit 60 automatically turns itself off as a function of time (with a conventional timer circuit or processor that keeps track of on or inactive time, etc.), or as a function of temperature, with a temperature sensor included in base unit 60. As in the illustrated embodiment a light source or lamp in provided in base unit 60, such implements serve to prevent the lamp from staying on for an indefinite period of time, and reduce the risks of thermal damage, fire or the like. Display 59 preferably is provided to display color measurement data, predicted shades or the like, as will be described in greater detail hereinafter.

In operation, a use preferably first applies barrier 50 (which may be considered an "infection control tip"), which is achieved by picking up handpiece 1 from its cradle and applying barrier 50, such as previously described. An exemplary screen shot of display 59, which reminds the user to apply barrier 50, and calibrate the instrument with the barrier in position, is illustrated in FIG. 9. What is important is that the user be provided a reminder, and preferably interlock, so that the instrument cannot be operated without calibration, and preferably without calibration with the barrier properly secured to the instrument. In preferred embodiments the instrument is calibrated by being positioned in cradle 55 with barrier 50 in position, and then being rotated about the axis of arm 55A so as to come into contact with calibration block 56. Guide 57 is optionally provided to more reliably guide the tip of handpiece 1 so as to land in a center portion of calibration block 56 (calibrating near an edge of calibration block 56 is undesirable, and guide 57 is provided to reduce this possibility).

Preferably, an in contrast to typically opaque calibration standards of conventional systems, calibration block 56 is a translucent or semi-transparent material, and preferably is chosen to have optical properties (such as color, translucency or the like) that is substantially in a middle portion of the range of optical properties for the particular materials that are to measured. For example, for a dental application, the optical properties of calibration block 56 preferably are an off-white shade and translucent, roughly in the middle of color and translucency values of normal human teeth. Having such a calibration block, rather than calibrating at an extreme of an optical range (such as pure white or pure black, etc.), has been determined to give more advantageous results. This has been determined to be particularly true for translucent materials such as dental objects. Without being bound by theory, it is believed that calibrating with a translucent material, for example, can help calibrate out effects of "edge loss," which is understood to be a problem with conventional measurement techniques for translucent materials, etc.

Also in accordance with the present invention, calibration block 56 (it should be noted that calibration and normalization in this context may be generally considered synonymous) used for calibration may be removable and cleanable, such as by autoclave cleaning. Preferably, calibration block 56 is sufficiently durable, an exemplary material being porcelain, so as to be wiped clean or autoclaved repeatedly, without substantial degradation of optical properties. In certain embodiments and operative environments, where degradation of the optical properties of the calibration block may be of concern, a two step calibration/normalization process is applied. At a first point in time, a reference standard of known optical properties is measured. This "gold standard", which may be provided with the known optical properties (which may be loaded into the instrument and stored), is measured with the instrument (the "gold standard" is then secured and stored in a manner to minimize any degradation of optical properties). Calibration block 56 is then measured. Based on the gold standard optical properties data (known/entered and measured), and based on the measurement of the calibration block, a first set of calibration/normalization data is created. During normal operation, preferably prior to each use of the instrument, the calibration block is measured again, and based on a comparison with the first set of calibration/normalization data, a second set of calibration/normalization data is created. This second set of calibration/normalization data is preferably used to adjust the data resulting from normal operational measurements. Periodically, such as after a period of months, the gold standard may be measured again, and an updated first set of calibration/normalization data is created, etc. With such a process, changing optical properties of the calibration block, which would not be expected to change rapidly, and also be calibrated out.

It also should be noted that, in accordance with the present invention, a single calibration measurement may be used even though different types of materials may need to be measured. As previously described, for example, a dental professional may desire to measure a natural tooth and a restorative material tooth on the same patient. In accordance with the present invention, a calibration measurement is performed, which is independent of the type of material being measured. Thus, even though different shade prediction algorithms or the like may be utilized to carry out the shade prediction process (as previously described), a single calibration measurement may be conducted prior to measuring both types of materials. This is important in that, after measuring either the tooth or restorative material in the patient's mouth, a contamination risk is presented if the calibration block needs to be touched again prior to measuring the second material. In accordance with the present invention, only one calibration measurement needs to be made for measuring both types of materials.

Returning again to the calibration process as part of the normal operation of the instrument, in preferred embodiments a switch internal preferably internal to base unit 60 is activated as handpiece 1 in cradle 55 is rotated in position for the tip to be positioned in the middle of calibration block 56. In such embodiments, the instrument automatically knows that it is to enter calibration mode, and thus take a calibration measurement and generate calibration data accordingly. In alternative embodiments, calibration mode is entered upon first turning on the system or before taking a measurement, and the user must start the calibration measurement by depressing the switch (such as switch 51 of FIG. 7A) on handpiece 1. This may be a dual switch mode, where a first switch activated by the rotation of cradle 55 about the axis of arm 55A indicates to the system that it is calibration mode, while the second switch (e.g., switch 51) is activated by the user when he/she has observed that the tip of the probe is positioned in a center portion of calibration block 56. In either case, in preferred embodiments, the instrument will not operate without calibration measurement having first been performed.

It also should be noted that such a calibration measurement serves to normalize the instrument and calibrate out effects due to lamp drift, aging of fiber optics, optical couplers, filters and other optical components and the like, as well as to normalize the electronics and produce a "black level," such as described in the Referenced Patent Documents.

Figure 9A:
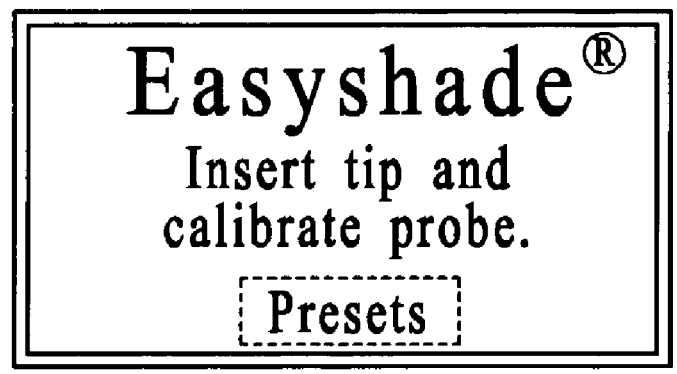
FIGS. 9A-9G illustrate exemplary display screens that may be utilized in accordance with the present invention.

It also should be noted from FIG. 9A that display 59 preferably is covered by a touchscreen so that "soft switches" may be provided, which are activated by the user touching the touchscreen over an icon or displayed button. In FIG. 9A, the presets button may be activated in order for the user to put the instrument into a mode whereby system settings (such as brightness, volume, data display options, etc.) may be changed.

Figure 9B:
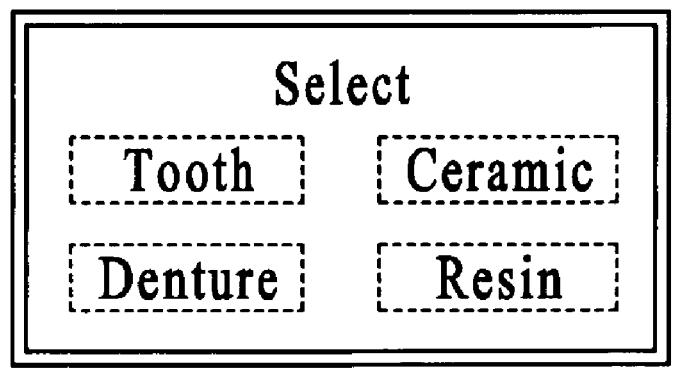

Referring to FIGS. 9B to 9G, additional exemplary screen displays will be described. FIG. 9B illustrates a screen display by which the user may inform the system of the type of material being measured. As previously described, in certain embodiments the operation of the system (e.g., the manner of making shade predictions, etc.), may be optimized depending on the type of material. This is accomplished by touching the touchscreen at the appropriate portion.

Figure 9C:
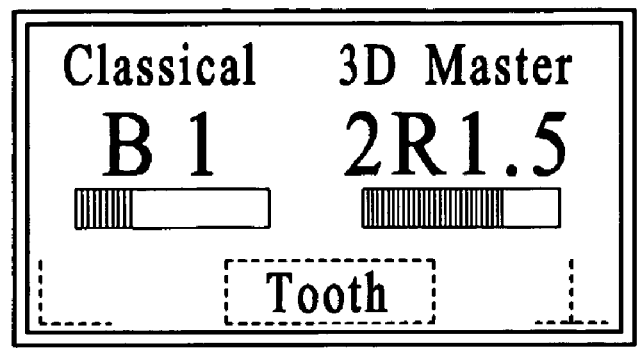
Figure 9D:
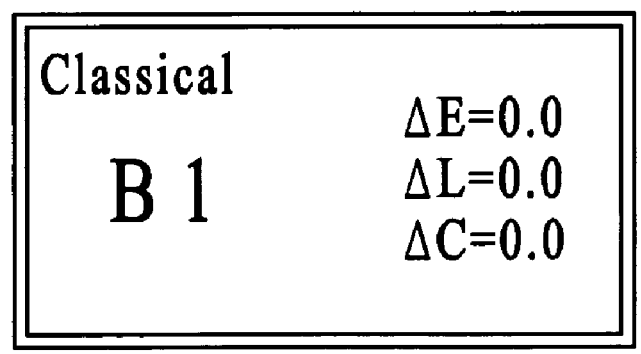

As illustrated in FIG. 9C, the results of a data measurement may be conveniently displayed on display 59 as illustrated. In preferred embodiments, the output, particularly for the dental application, consists primarily of a display of one or multiple shade guide values (examples of the well-known Vita Classical and 3D Master shade guides are illustrated in FIG. 9C). In such embodiments, whether one two (or other number) of closest match color or shade values is output is a user selectable feature, such as via the preset button discussed in connection with FIG. 9A). In preferred embodiments, the type of material being measured also is displayed, such as is illustrated. What is important from FIG. 9 is that, although a very sophisticated set of measurements were made as part of the process, the output may be a simple shade or color value (or values), in a form that is readily understand or useable by the particular user. For example, the display could display Pantone colors or shades, paint formulations, pass/fail results, etc.

Also in preferred embodiments, while a standard display may show an output of reduced form (such as the simple color or shade value of FIG. 9C), additional color or spectral information also may be provided. For example, a spectral plot icon is displayed (such as illustrated at the lower left corner of the screen shot of FIG. 9C), and upon touching of the icon a reflectance spectrum of the object that was measured is displayed (see, e.g., FIG. 9F for such a spectral reflectance plot, which plots relative energy as a function of wavelength). In another example, a user may touch the Vita Classical shade guide value of FIG. 9C, and the display then presents additional information, such as the deviation from the "true" color of the displayed closest match. In another example, the Vita 3D Master shade guide value of FIG. 9C may be touched, and the user then additional information regarding the measurement result relative to value, chroma and hue in the Vita 3D Master system (see, e.g., FIG. 9E). In still another example, an "L a b" icon may be displayed (such as via the icon shown at the lower right corner of FIG. 9C), and upon touching an L a b plot may be displayed (see, e.g., FIG. 9G). What is important, and what may be appreciated from the foregoing, is that the results of the color measurement/spectral analysis process be presented in a form desired by the particular user, with a point and touch operation enabling particular users to "get behind the data" and be presented with more color/spectral data, and more color/spectral data of the form that is most desired by the particular user, etc.

In certain alternative embodiments, whether the output is a single or multiple shade guide values or colors (such as the multiple shade guide system values illustrated in FIG. 9C), the closest match may be a value in one system or the other. In certain embodiments, a confidence barrier is displayed before the displayed shade guide or color values, as illustrated in FIG. 9C. In the particular illustrated example, the closest match of the 3D Master system was determined by the instrument to be a closer match than the closest match in the Vita Classical system, which is evidenced by the larger confidence bar below the displayed Vita 3D Master value. While the confidence bar display is exemplary, what is important is that, in such embodiments, a visual indicator be provided so that the operator may determine some degree of closeness of the match. With a low confidence indicator, for example, the user may then decide to get additional color data (such as previously described) to supplement the closest match value that is displayed, etc.

Figure 10:
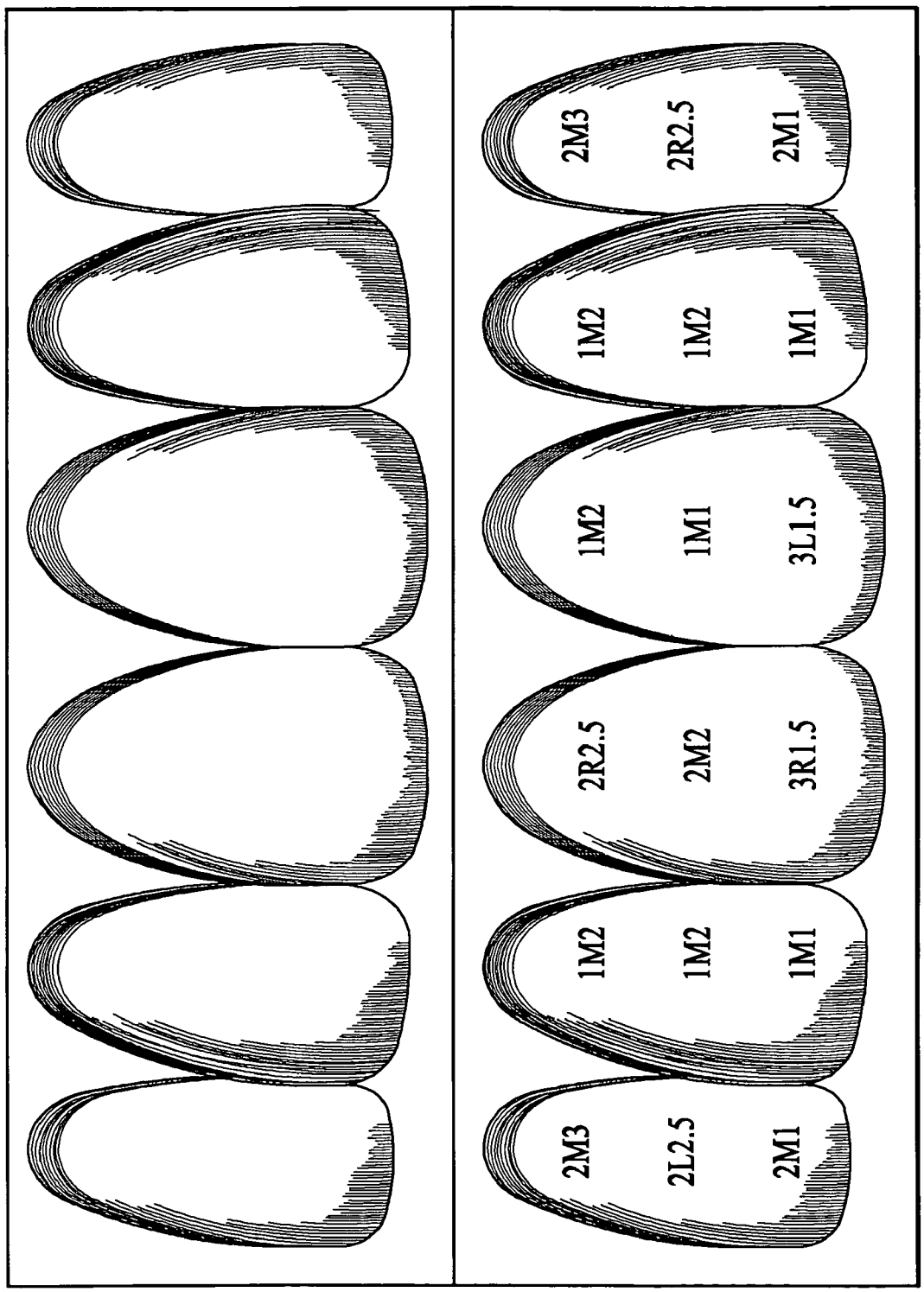
FIG. 10 illustrates an exemplary multi-camera image display, with superimposed shade data, in accordance with an exemplary alternative preferred embodiment of the present invention.

As described in the Referenced Patent Documents, data from spectrometer/spectrometer may be combined with an image from a camera. This can particularly be true in the context of dentistry, where often a shade assessment is a precursor to getting a restorative tooth produced. While the shade information is of particular importance to producing an aesthetically pleasing restoration, supplementing the shade information via a camera image also be useful to the dental professional or technician or other person involved in the process. With the present invention, a single or multiple areas of a tooth may be measured. Via the touch screen the user, for example, may indicated to the instrument that one or multiple areas are to be measured. Thereafter, the user may then measure the one or multiple areas of the tooth. With a camera (such as a standard digital camera), an image of the tooth or teeth may be captured. Data captured with the image may be imported into a computing system that also receives the image from the digital camera. The measured shade data may then be superimposed onto the image from the digital camera, such as is illustrated in FIG. 10. Also as illustrated in FIG. 10, two images may be combined. One image may contain multiple shade values (or single shade values), which shows at which spot on the tooth (or teeth) the measurements (or measurement) were/was made. A second image may contain no superimposed shade data. With such a multi-image, superimposed display, the person preparing the restorative tooth, for example, may see an image with real shade/color data superimposed on the area of the tooth from which the data was collected, yet may also see an image with no superimposed shade or color data.

Figure 9E:
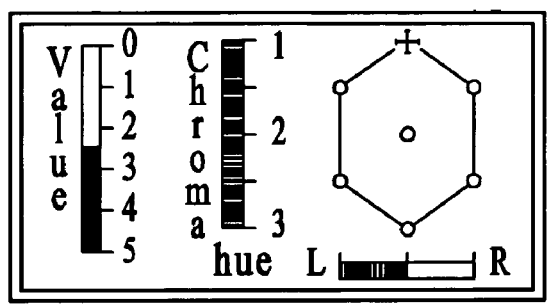
Figure 9F:
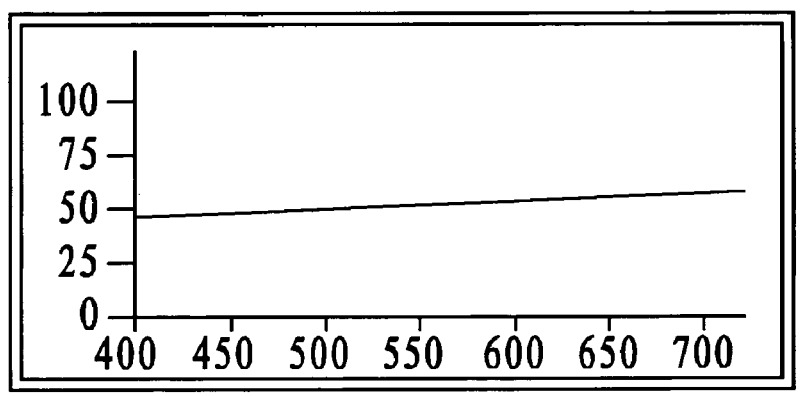
Figure 9G:
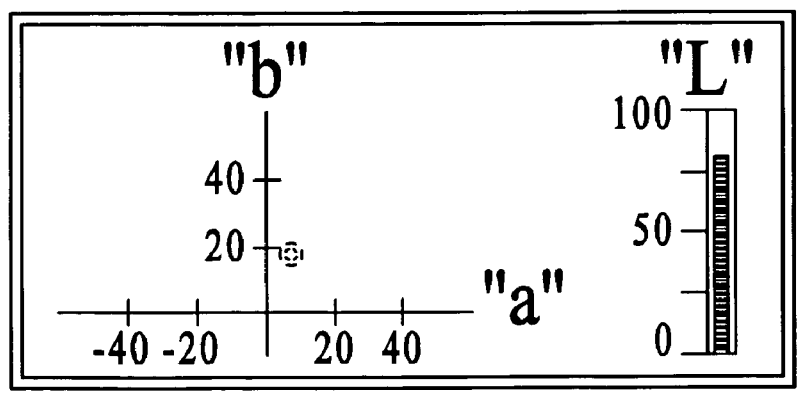

In other embodiments, the shade or color data may be selectively superimposed or not superimposed (which may be performed with only a single image of the camera displayed, and which may be activated by mouse/click operation, pull down menus or the like). In yet other embodiments, a single or multi-image is displayed, with shade data superimposed, and with additional color or spectral data displayed (such as is illustrated in the displays of FIGS. 9E-9G) upon further command. In one example, the user may click the area of the tooth and a superimposed shade value is displayed; in a subsequent click of the shade value, additional color or spectral data is displayed. In such embodiments, for example, subsequent clicks scroll through the various shade/color/spectral data options so that the user may display the type and level of information that he/she may desire in the particular situation.

As described in the Referenced Patent Documents and the foregoing description herein, various apparatus, methods and methodologies for measuring the optical properties of teeth and other materials may be provided in accordance with embodiments of the present invention. The optical properties can consist of reflectance color, translucency, gloss, pearlescence and other optical parameters of materials that affect the manner in which incident light is reflected from or returned from a material to a light receiver or human eye. As a general matter, all of the optical properties of a material are utilized by the human eye and brain to distinguish a material from other materials and are used to identify or otherwise classify a material.

One principal object of certain preferred embodiments of the present invention is to quantify the optical properties of, or to shade match, teeth. Thus, for purposes of convenience the following description focuses on shade matching of teeth or other dental object. It should be understood, however, that such embodiments of the present invention also may be applied to other materials, including, but not limited to, paint, ink, precious gems, glass materials, plastic materials, construction materials, etc.

Traditionally, teeth are shade matched by visually comparing a tooth to a set of "shade guides". The shade guides typically are constructed to visually appear the same as teeth and are constructed of materials that tend to simulate the appearance of teeth. There are a number of commercially available shade guides today, and the shade guides typically relate to or can be referenced to a recipe for producing a dental restoration. Typical examples of commercially available shade guides are the Vita Classical (16 shades), Vita 3D-master® (29 shades), Bioform® Truebyte® Color Ordered™ Shade Guide (24 Shades), Ivoclar-Vivadent Chromascop (20 Shades). As a general matter, one determines the preferred "color" of a restoration by holding a shade guide sample next to a neighboring tooth and visually comparing and choosing the shade guide that most closely matches the tooth to be matched.

Difficulties with traditional shade matching have been discussed in the literature. One difficulty is that of controlling the ambient light, which affects the color of both the shade guide and the tooth (often in a non-linear manner). Another issue is the variation in color perception of humans. Another issue is eye fatigue. Yet another issue is the variation in quality control of shade guides or the age or color deterioration of shade guides.

In accordance with certain preferred embodiments of the present invention, methods and systems are provided to match the optical properties of teeth (or other object) and to choose a corresponding shade guide match, in which optical properties of the tooth are measured with a spectrophotometer (or other color measuring implement) and match the optical measurements with the optical measurements of shade guides or restorative dental materials. One such instrument that measures the optical properties of teeth is known as the Vita Easyshade®. Aspects of the operation of such an instrument have been disclosed in the Referenced Patent Documents and elsewhere herein.

Traditionally, shade matching of optical measurements is made based upon ΔE, where:

$$\Delta E = \sqrt{\{\Delta L^2 + \Delta a^2 + \Delta b^2\}}$$

and where the parameters L, a, b are the tristimulus CIE L*a*b readings of a color measurement. The CIE L*a*b parameters typically are calculated for an optical measurement and a ΔE typically is calculated for each shade. The best shade match typically is determined to be the shade with the lowest ΔE.

There are difficulties with such ΔE shade matching, particularly for materials such as teeth which have low chromacity and small variations in hue (the polar coordinate angle of a chromacity a, b plot). The ΔE calculation in general gives equal weight to value and chromacity variation. In certain cases, a variation in L of, for example, 3 units may be difficult to detect while a variation of 3 units of a, b may be quite distinguishable, and vice-versa. ΔE shade matching also tends not to distinguish whether colors are more or less saturated from one another. Often when attempting to match the shade of a tooth to a shade system such as the Vita Classical shade system, several shades Will be nearly equally spaced from the measurement, resulting in more than one "best shade match". ΔE shade matching typically cannot resolve the conflicts under such circumstances.

In accordance with such embodiments of the present invention, an optical measurement is made of a tooth or other dental (or other) object. Such a measurement may be made as described elsewhere herein and/or in the Referenced Patent Documents, but the presently described embodiments are not limited to such particular measurement techniques. The resulting measurement of the tooth is converted to a plurality of color parameters. In accordance with one preferred embodiment, 11 color parameters are calculated and preferably consist of the following (in accordance with other embodiments, a different number of parameters are utilized, which may include various combinations of the following).

X, Y, Z—color tristimulus values.

L, a*, b*—CIELa*b* calculated from X, Y, Z, hereinafter referred to as L, a and b.

C, h—Chromacity and hue—polar coordinate representations of a, b.

I—Integral intensity of the spectrum.

$1^{st}$—Integral intensity of the absolute value of the first derivative of the spectrum (degree of curvature).

$2^{nd}$—Integral intensity of the absolute value of the $2^{nd}$ derivative of the spectrum (degree of curvature change).

where:

$$I = \int_{400}^{700} S(\lambda)d\lambda \approx \sum_{i=1}^{n} S_i$$

where $S_i$ is the intensity of a spectral band and n=number of bands of the spectrometer or other color measurement device.

and where $$1^{st} = \sum_{i=1}^{n-1} \text{abs}(S_{i+1} - S_i) = \sum_{i=1}^{n-1} \text{abs}(\Delta S_i)$$

and $$2^{nd} = \sum_{i=1}^{n2} \text{abs}(\Delta S_{i+1} - \Delta S_i)$$

In accordance with certain preferred embodiments, prior to making an optical measurement, a table of parameters is developed and stored in memory for each shade. The parameters preferably consist of a minimum value, a preferred value, and a maximum value for each parameter. Thus, in accordance with such preferred embodiments of the present invention, there may be, for example, 11 times 3 values stored for each shade in a shade system, or, for example, 33×16 values (528) for the Vita Classical shade system, 33×29 values (957) for the Vita 3D-Master system, and so on for other shade systems. For an instrument to hold, for example, four known tooth shade systems it would need to store about 2937 numbers, which has been determined to consume a relatively small amount of memory for modern microprocessor or microcontroller-based systems.

In accordance with such embodiments, the minimum parameter for a shade is the lowest acceptable value of the parameter for a shade to be considered a "shade match;" the maximum parameter is the maximum acceptable value of the parameter for a shade to be considered a "shade match;" and/or the preferred parameter is the preferred value and may or may not be the mid point between the minimum and maximum values. Each of the 11 (or other number) parameters preferably is given a hierarchy, preference and weight. It has been determined that some of the parameters preferably are considered more important than others, and thus are weighted higher and are given a higher preference, while others are weighted lower. In accordance with certain embodiments, certain parameters must match, while others may or may not be matched in order to choose the best shade match. Thus, in accordance with such embodiments, in addition to the minimum, maximum and preferred parameter values, each parameter for each shade preferably is assigned one or more of the following:

Must match—The measured parameter must be between the minimum and maximum in order for the shade to be considered a candidate shade.

Delta weight—A weighting factor is applied to each parameter delta calculation, where the delta is the absolute value of the difference between the preferred parameter value and the measured parameter value.

In accordance with certain preferred embodiments, shade matching is a process of elimination that proceeds as described below and as illustrated in the flow chart of FIG. 11. In accordance with preferred algorithm 70, an optical measurement is made of the tooth or other object (step 72), and the color parameters are calculated (step 74). The parameters are then compared with the minimums and maximums of each shade in the shade system (or systems) and a table is tabulated for each shade (step 76). Preferably included in the table are:

$H[s]$ = Number of hits for shade [s].

= Number of parameters for shade [s] that are in the range:

minimum< measured parm < maximum where: 1<=s<=number of shades.

In accordance with preferred embodiments, to be considered as a candidate for a shade match, all of the parameters that must be matched (i.e., are in the range of minimum<measured<maximum) are grouped. Shades that do not match all of the parameters that must be matched are eliminated from consideration (step 78). If no shade matches all of the parameters that must match, then a failure is reported (steps 84 and 86; note that the precise ordering of illustrated steps is exemplary). Note that, in accordance with certain alternative embodiments, if a shade matching system must always choose a shade even if the variations from all shades are large, the "must match" condition can be ignored. For certain shade matching applications and embodiments, this may be desirable. After the shades that meet the "must match" criteria are grouped they are additionally grouped in order of maximum to minimum number of hits. If only one shade satisfies the "must match" criteria, or if there is one shade with a greater maximum number of parameter hits, then this shade is the chosen shade (steps 80 and 82).

Often more than one shade will have the same greatest number of hits for a particular measurement, and the number of hits will be less than the maximum number possible which is the total number of parameters considered (or 11 tin the preferred embodiment). In accordance with preferred embodiments, the shades with the same number of "hits" are further evaluated by calculating the following (step 88):

$SW[s]$ = Sum of weighted deltas for shade [s].

$$= \sum_{i=1}^{n} W_i \Delta P_i$$

where: n=number of parameters
$W_i$=weight of parameter i
$\Delta P_i$=abs(measured parameter—shade preferred)

$SCW[s]$ = Sum of common deltas for shade [$s$].

$$= \sum_{i=1}^{c} W_i \Delta P_i$$

where: c=number of common parameters—(see below)
$W_i$=weight of parameter i
$\Delta P_i$=abs(measured parameter—shade preferred)

$SUW[s]$ = Sum of uncommon deltas for shade [$s$].

$$= \sum_{i=1}^{u} W_i \Delta P_i$$

where: u=number of uncommon parameters—(see below)
$W_i$=weight of parameter i
$\Delta P_i$=abs(measured parameter—shade preferred)

In accordance with preferred embodiments, the common and uncommon deltas preferably are evaluated by grouping all shade parameters into two groups. The common delta group is for parameters that are a match for all shades under consideration. The uncommon delta group is for the remaining parameters—i.e., those that are not common. After calculating SW, SCW and SUW for each shade under consideration, the sum of the weighted deltas preferably is evaluated first. If it is less than a predetermined number (d1) for one shade and if all the other shades under consideration are greater than another predetermined number (d2), then the shade is the selected shade (steps 90 and 92).

If none of the shades under consideration have an SW less than a predetermined number (d1) or if another shade or plurality of shades under consideration have SW's that are less than a second predetermined number (d2), then the sum of uncommon deltas preferably is considered next. Again, if one shade has a SUW less than a predetermined number (ud1) and all the other shades under consideration are greater than a second uncommon delta number (ud2), then the one shade is the selected shade match (steps 94 and 96).

If none of the shades under consideration have an SUW less than a predetermined number (ud1) or if another shade or plurality of shades under consideration have SUWs that are less than a second predetermined number d2, then preferably the final decision is based upon the sum of common deltas SCW. The shade with the lowest sum of common deltas SCW preferably is the selected shade match (step 98).

Lastly, in accordance with preferred embodiments the sum of weighted deltas SW of the chosen shade is compared to a final acceptance table to determine the quality of the shade match (step 100). If it is less than a predetermined number, then the quality of the match is reported with a table of match levels to the predetermined number. In accordance with one preferred embodiment of the present invention, three levels of quality are reported preferably consisting of "good", "fair" and "poor" (in accordance with other embodiments, other descriptive/qualitative labels are utilized). If the sum of weighted deltas SW is less than a first predetermined number for "good," the shade match is reported to be a "good" match. If the sum of weighted deltas SW is greater than the number for "good" but less than the number for "fair," then the shade match is reported to be "fair," and if neither of the foregoing two conditions are met, then preferably the shade match is reported to be "poor." In other embodiments, more or less than three levels of shade match quality are reported.

Other aspects of certain preferred embodiments will now be described. Certain shade system permit interpolation of shades. As an example, the Vita 3D-Master system is designed to report a Value (L), Chroma and hue. There are six levels of value ranging from the highest (0) to the lowest (5). Chroma ranges from 1 to 3 and hue is reported as L, M and R. It is possible to prepare ceramic restorations whose value and chroma are interpolated by 0.5 (½ of a value or chroma group) by mixing 50%-50% proportions of materials from bottles of each shade group.

In accordance with preferred embodiments of the present invention, interpolation of Vita 3D-Master shades (or other shade system shades) is done by first determining the best shade match, preferably as described elsewhere herein. Once a preferred shade match is selected, preferably the value and chroma parameters of the measurement are compared to the preferred parameters of the shade and are also compared to the preferred parameters of the neighboring 3D-Master shades. If the value parameter is greater than the value parameter of the preferred shade, then it is also compared to a value parameter calculated from the next higher value shade with the same or comparable chroma and hue. Thus, if 3M2 is the selected shade and the measured value is determined to be higher than the preferred value for 3M2, then it is compared to the average of (or mid point of) the values of 3M2 and 4M2. If the measured value is greater than the mid point value, then the reported value is increased by 0.5, or the value will be 3.5.

A similar calculation preferably is made for chroma. The measured chroma preferably is compared with the preferred chroma of the selected shade and the chroma is increased or decreased by 0.5 if the measured chroma is greater than or less than the chroma average of the neighbor shades. In other shade systems where hue may be quantified numerically, a similar calculation preferably is made for hue.

As will be appreciated by those of skill in the art, such preferred shade matching algorithms as described herein for dental materials are applicable to additional parameters such as translucency, pearlescence or gloss.

Additional details of exemplary operational aspects of additional embodiments of the present invention will now be described.

In accordance with certain preferred embodiments, the user may desire to measure a single area of a tooth (or other object), or a plurality of areas. In embodiments where a display and touchscreen are utilized, for example, the single or plural area measurement mode may be selected by touching a window, button or icon on the display (with the touchscreen serving as the data input device, as will be understood by those of skill in the art) (the presently described embodiments should be understood to not be limited to such display/touchscreen implementations). Preferably, the user indicates that he/she desires to make a plurality of measurements by user input to the system, and the system operates in a mode in order for multiple measurements to be made. In other embodiments, the system enters into a multiple measurement mode by default, factory setting or the like.

In accordance with such embodiments, the system via the display device provides a graphic indication that multiple areas are to be measured. Thereafter, the user makes a measurement of a predetermined area, and preferably the unit then displays the predicted best match of the shade of the measured area. The user may then proceed to measure other areas, with each measurement preferably being followed by a display of the closest match to a shade in a shade guide type of system.

Figure 12:
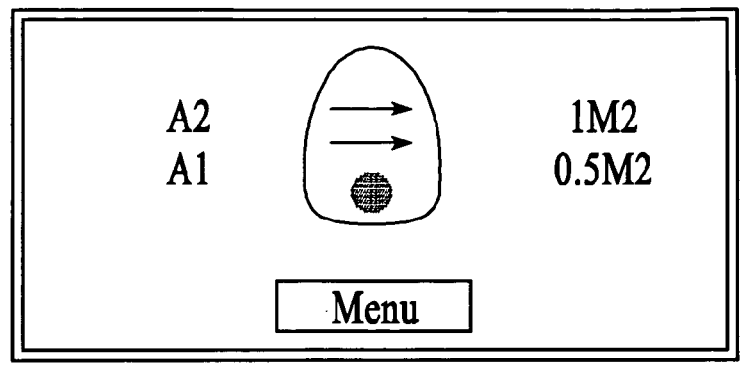
FIG. 12 is an exemplary screen display illustrating measurement of multiple areas of an object in accordance with certain embodiments of the present invention.

FIG. 12 illustrates an exemplary screen display for a dental application/embodiment. In the illustrated example, the system measures three areas of the tooth, from top to bottom; in alternative embodiments, there may be a different number of areas, and they could be a arranged in a different manner, such as a grid pattern, for example, as will be appreciated by those of skill in the art. Continuing with the illustrated example, in accordance with preferred embodiments, the system compares the data from the measurement to a plurality of shade guide systems; in the illustrated example, utilization of two shade guide systems is illustrated, the Vita Classical system, and the Vita 3D Master system. In accordance with such embodiments, after the first/top area is measured, the system confirms whether the measurement is valid, and if so predicts and displays the best/closest match for the two shade systems. In FIG. 12, this is illustrated by the top most A2(Vita Classical) value displayed on the left of the screen display, and the top most 1M2 (Vita 3D Master) value displayed on the right of the screen display. In preferred embodiments, such display is accompanied by a visual indicator of which of the best/closest matches of the multiple shade guide systems is the best match. In the illustrated example of FIG. 12, for the first/upper area measurement, the closest Vita Classical shade was determined to be an A2, and the closest Vita 3D Master shade was determined to be a 1M2. The arrow in the upper area of tooth illustration pointing towards the 3D Master shade guide value 1M2 provides an indication that, in this example, the 1M2 shade is predicted to be a closer match to the measured area as compared to the closest Vita Classical shade, which is A1. As a result, a user or practitioner (dental lab technician or otherwise), can be presented visually with multiple shade guide values of the closest matches to the measured area in a concurrent manner, while also being presented visually with an indication of which of the multiple shade guide system values represented the best match.

Continuing with the example of FIG. 12, a second measurement of the tooth, in this example, the central area, resulted in a best/closest match prediction of A1 in the Vita Classical system, and a best/closest match prediction of 0.5M2 in the Vita 3D Master system. In the illustrated example, again the 3D Master value of 0.5M2 was predicted to be a closer match than the closest Vita Classical system value of A1(again, this is exemplary only, and for other exemplary measurements a Vita Classical shade could have been the closest match). The process may then continue for the third area of the tooth to be measured, in this example the bottom area, with the closest match values being displayed after the third measurement. In the exemplary screen display of FIG. 12, however, the third area has not yet been measured, and the displayed dot or circular area presents a visual indication of the area to be next measured.

What is important from the foregoing is that multiple areas of a tooth or other dental object (or yet other object) may be measured, with a prediction of the closest match in multiple shade guide or color systems being concurrently made, and preferably with an indication of which of the shade guide or color system values represented the closest match for each of the particular measurements. It will be understood, however, that such a multiple shade guide/color system technique could be applied for a single measurement, or for plural measurements of a different number or positional arrangement of measured areas, etc.

While not expressly illustrated in FIG. 12, if it is desired to re-measure a particular area, in accordance with preferred embodiments the particular area on the displayed tooth may be touched, with the exemplary arrow being replaced by the exemplary dot or circular area (or other visual indicator of the particular area to be re-measured). This may thereafter be followed by a re-measure of the particular area, which is preferably followed by a display of the closest matches and best match, such as previously described. In addition, as described elsewhere herein and in the Referenced Patent Documents, additional color or other optical characteristics data could be displayed, which could be achieved by touching the touchscreen, for example, on the displayed shade data, which may then be followed by presentation of additional color information, etc.

In accordance with preferred embodiments of the present invention, a tooth or other dental object (or other object) may be measured (in a single or multiple areas), with the resulting shade guide value or color data used to fabricate another object of similar optical characteristics. In the field of dentistry, this typically is referred to as a "dental restoration." While the present invention is not limited to dental restorations, the following description of certain alternative embodiments will be made with respect to a dental restoration.

One way to check the quality of a dental restoration is to simply measure the dental restoration with an instrument, which may be the same or different instrument that measured the original tooth to which the restoration is to be a match. For example, if the original tooth that was measured was a 3M2, a restoration that was produced and intended to match this original tooth could be measured; if the closest match for the restoration was a 3M2, then it could be considered a good match; if the closest shade for the restoration was not a 3M2, then it could be considered not a good match.

One problem with this approach is that it could result in false reporting of "not a good match," for example. In many shade guide systems, the particular shades may be close together when considered in view of the shade perception abilities of a typical human observer. In accordance with the present invention, even though a restoration may be measured and have a different closest shade guide value as compared with the originally measured tooth, it may still be a very acceptable match to the original tooth to a human observer, and may be recognized or predicted as such by the system.

In accordance with embodiments of the present invention, a user such as a dental technician or doctor may extra-orally verify that a shade restoration is an acceptable match to the prescribed or intended intra-oral shade. Referring to FIGS. 13A-13D, exemplary screen displays for such a process will now be described.

Figure 13A:
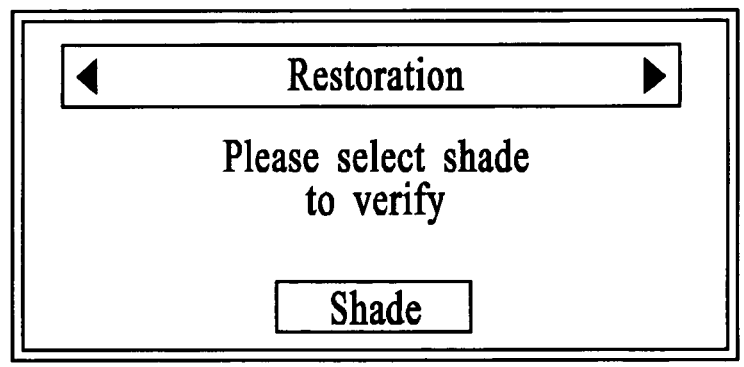
FIGS. 13A-13D are exemplary screen displays illustrated a restoration verification process in accordance with certain embodiments of the present invention.

To verify a restoration, a user may select "Restoration" such as via touchscreen input, as illustrated in FIG. 13A. Rather than simply have the user measure the restoration, however, the system, as illustrated in FIG. 13A, prompts the user to input the shade that the restoration is intended to match. Thus, in accordance with such embodiments of the present invention, a first step in verifying a restoration is selecting the prescribed or intended shade.

Figure 13B:
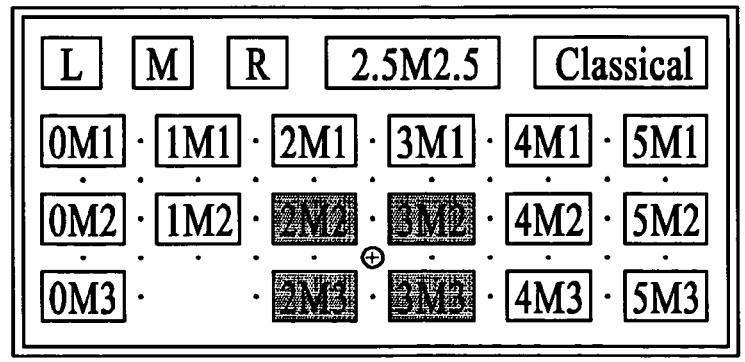

In certain embodiments, touching the "Shade" selection area of the screen of FIG. 13A causes the display of FIG. 13B to be displayed. As will be appreciated, the screen of FIG. 13B provides for the input of exemplary shade guide values from the Vita 3D Master system, but other shade guide systems similarly could be utilized; for example, with the illustrative screen provided in FIG. 13B, a box is provided labeled "Classical," activation of which would enable a user to input a shade via the Vita Classical shade system. It should be understood, however, that other shade systems could be utilized, and other implements for selecting a particular shade guide system also could be utilized.

The screen illustrated in FIG. 13B allows the selection of a particular prescribed or targeted Vita 3D Master shade, preferably including interpolated shades, as illustrated (it being understood, for example, that intermediate shades could be achieved by mixing Vita 3D Master porcelains, such as in a manner known in the art). Preferably, this particular shade guide value selection is achieved by touching the screen and moving a finger either to a particular Vita 3D Master shade or over points midway between two or four shades in the manner illustrated. In the exemplary illustrated screen of FIG. 13B, a user may first touch one of the three boxes in the top left of the screen to select a particular hue (L, M or R). In the illustrated example, the M hue has been selected. Then the user may touch the screen at a point that corresponds to the target interpolated 3D Master shade guide value. Removing the finger from the touch screen preferably will select that shade. In the illustrated example, the selected position is midway between value groups 2 and 3, yielding a 2.5 value group. Similarly, the selected chroma position is midway between 2 and 3, yielding a 2.5 chroma.

What is important is that the user be provided an intuitive, easy manner to input a shade guide value which represents the closest shade guide value of the original measurement (i.e., the prescribed or target shade for the restoration); in accordance with the present invention, however, it has been determined that, in environments such as dental operators, the graphical touch screen method provides substantial benefits, as the dentist or other user may be wearing gloves, etc., and may find it undesirable to manipulate typical computer data entry devices, such as a keyboard or mouse, etc. In alternative embodiments, however, the prescribed or target shade guide value may be made available to the system via other user input, may have conveyed to the system electronically via a data connection, or may have been stored in the system from the original measurement (in the later alternatives, color data in addition to or in lieu of a shade guide value may be conveyed to or stored in the system for purposes of assessing the restoration acceptability, etc.).

Figure 13C:
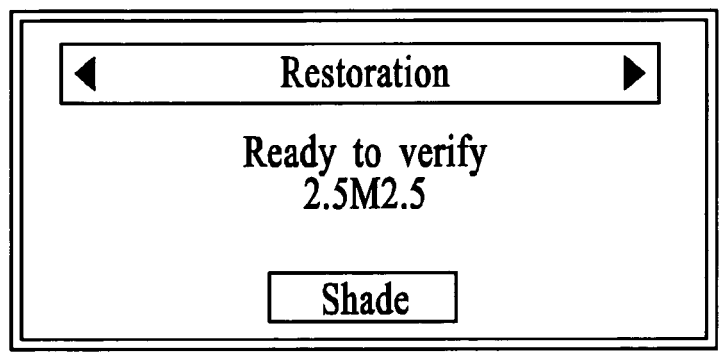
Figure 13D:
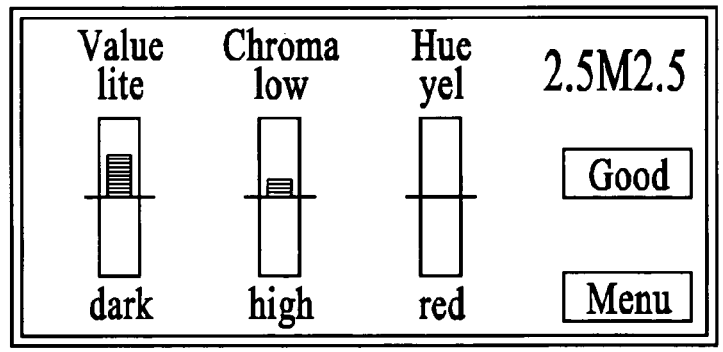

Assuming that a Vita 3D Master shade has been entered as the prescribed shade for the restoration, the screen illustrated in FIG. 13C preferably is displayed. This screen provides visual feedback to the user of the prescribed or intended shade of the restoration, while also prompting the user to measure the restoration. After measurement of the restoration, a screen such as illustrated in FIG. 13D preferably is displayed. In the illustrated example, the horizontal lines under "Value", "Chroma" and "Hue" preferably indicate the nominal values for the target shade. The exemplary illustrated screen indicates that the restoration is a good match to the prescribed shade (2.5M2.5), with the Value (or lightness) of the restoration being slightly lighter than the target shade, the Chroma (the saturation of the color) of the restoration being slightly lower than the target shade, and the Hue (color) of the restoration very closely matching the target shade. Touching the shade match quality predictor button, which is illustrated as "Good" in the example of FIG. 13D, in certain embodiments preferably causes the display of additional information on the accuracy of the measurement in color space (exemplary color space screens have been previously described herein).

While the example of FIG. 13D predicted that the restoration would be a good match to a 2.5M2.5, in accordance with the present invention other predictive labels may have displayed, depending on the closeness of the measured shade of the restoration as compared with the prescribed or target shade. In one exemplary embodiment, the predicted shade match quality could have been evaluated as, for example, Good, Fair, or Adjust. In accordance with such embodiments:

1. "Good" means that an expert at shade matching may see little or no difference between the restoration and the target shade to which it has been verified.
2. "Fair" means that an Expert at shade matching may see a noticeable but acceptable difference between the restoration and the target shade to which it has been verified. For an anterior restoration, this may not be acceptable.
3. "Adjust" means that an Expert at shade matching may see a noticeable difference between the restoration and the target shade to which it has been verified, and that the restoration should be adjusted to be an acceptable shade match.

What will be appreciated from the foregoing is that, in accordance with such embodiments, rather than having a user make a judgment as to the visual acceptability of a restoration based on whether a measurement of the restoration results in precisely the same shade guide value as the original measurement of the tooth, the present invention instead assists the user by making a prediction as to acceptability of the restoration based on an input of the prescribed or target shade guide value (or data from the original color measurement, which was conveyed to or stored in the system, etc.). Such a prediction of visual acceptability could be implemented, for example, by an algorithm similar to that previously described with respect to shade prediction, with the label "poor" being changed to "adjust," etc. What is important is that, in accordance with such embodiments, the system attempt to predict visual acceptability, as opposed to simply outputting a shade guide value of the restoration, which may result in, for example, visually acceptable restorations being rejected as a result in a difference between a reported shade guide value for the restoration (as compared to the original tooth, etc.).

Exemplary systems/methods in accordance with the present invention include the following. A spectrophotometer system including: a probe tip including one or more light sources and a plurality of light receivers; a first spectrometer system receiving light from a first set of the plurality of light receivers; a second spectrometer system receiving light from a second set of the plurality of light receivers; a processor, wherein the processor receives data generated by the first spectrometer system and the second spectrometer system, wherein an optical measurement of a sample under test is produced based on the data generated by the first and second spectrometer systems. A method for determining a value of a shade guide system that is a closest match to the shade of an object, including the steps of: measuring the optical properties of the object with an instrument; calculating a plurality of color parameters based on the measurement; calculating a table of hits based on whether the color parameters satisfy predetermined conditions; determining whether one or more shades in the table of hits satisfies all corresponding "must match" conditions; if no shades satisfy all corresponding "must match" conditions then reporting a failure; and if multiple shades satisfy all corresponding "must match" conditions then assessing additional conditions to determine a best match shade. A method for determining optical characteristics of an object, including the steps of: measuring optical characteristics of the object with an instrument; determining a closest match to predetermined shade values in a plurality of shade guide systems; concurrently displaying the closest determined match in the plurality of shade guide systems; and displaying an indication of which of the concurrently displayed closest determined match in the plurality of shade guide systems is a best match. A method for determining visual acceptance of a restoration, including the steps of: storing data indicative of color characteristics of a plurality of shade guide values; measuring optical characteristics of an object to which the restoration is to be a visual shade match; determining a prescribed shade guide value for the restoration based on the measuring optical characteristics; fabricating the restoration based on the prescribed shade guide value, wherein constituent materials for the restoration are determined based on the prescribed shade guide values; entering or accessing the determined prescribed shade guide value for the restoration; measuring optical characteristics of the restoration; and providing a predictive indicator of the visual acceptability of the restoration as compared to the object based on the entered or accessed, determined prescribed shade guide value and data from the measurement of the optical characteristics of the restoration.

In accordance with alternative preferred embodiments of the present invention, additional improved shade matching algorithms are provided that preferably may used to shade match dental and other materials including with instruments as previously described and/or referenced herein. Such alternative preferred embodiments will now be described.

The inventors hereof have previously disclosed herein and in the Referenced Patent Documents various systems and methods for measuring color and other optical properties of materials and also for shade matching the results of the measurement and reporting the result in terms of a color reference or shade. In the context of the presently described embodiments, a principal purpose is to shade match teeth and other dental materials to, for example, the Vita Classical and Vita 3D shade systems. Thus, the following discussion focuses on shade matching teeth. It should be understood, however, that the principles disclosed herein also are applicable to other materials and shade systems, including, but not limited to, paint, ink precious gems, glass materials, plastic materials, construction materials, etc.

It is well known that a color spectrum can be converted to tristimulus color coordinates L, a, b, and that L, a and b can be mathematically written in their polar coordinate form as L, C and h where L is the "Value," C is the "Chromacity" and h is the "Hue." White materials have low chromacities (or chroma) while brightly colored materials have high chromacities. The hue or "tint" of the color indicates the degree of red, green or blue intensity. Generally, when chromacity is low, the importance of hue decreases, and as chromacity increases hue becomes increasingly important.

It has been determined that it generally is difficult for the human eye to distinguish and remember complementary changes in value and chroma. If the chroma of a material is decreased and if its value is simultaneously decreased, its appearance to a human observer may change little compared to the appearance that would occur for a comparable change of increasing value or chroma or decreasing value or chroma. One may increase value and chroma or one may decrease value and chroma over a fairly substantial range without significantly altering its appearance to the typical human observer.

The complementary L, C effect has been determined to be particularly important in teeth. Teeth generally appear white when they have low chroma, even when their value may be low compared to other teeth with higher value but also having higher chromacity. This effect combined with the effect that hue becomes less important as chroma decreases suggests that teeth be shade matched utilizing the complementary nature of value, chroma and hue.

Traditionally, shade matching of color is performed by calculating $\Delta E$ and determining the closest color match to be the shade with the lowest $\Delta E$ where $\Delta E$ is defined as the color variance of L, a and b:

$$\Delta E = \sqrt{\Delta L^2 + \Delta a^2 + \Delta b^2}$$

where $\Delta L$, $\Delta a$ and $\Delta b$ are the differences of the tristimulus coordinate measurement (M) to a shade(S):

$$\Delta L = L_M - L_S$$

$$\Delta a = a_M - a_S$$

$$\Delta b = L_M - b_M$$

In terms of L, C and h where $$C = a^2 + b^2$$

$$h = atan(a/b)$$

$$\Delta E = \sqrt{\Delta L^2 + \Delta C^2 + 2 C_M C_S \{1 - \sin(h_M)\sin(h_S) - \cos(h_M)\cos(h_S)\}}$$

$$\approx \sqrt{\Delta L^2 + \Delta C^2} \text{ as } \Delta h \text{ approaches } 0.$$

A difficulty with $\Delta E$ shade matching is that it does not distinguish the direction of the color change. Both $\Delta L$ and $\Delta C$ may increase if the measurement departs from the shade, yet visually its appearance may change little.

An additional problem arises from shade systems that do not evenly cover color space. Teeth, for example, are limited to a small region of the overall L, C and h color space and the Vita Classical shades are clustered into several areas. This often occurs in shade systems developed over a period of time where the number of shades is limited and where shades are concentrated in areas of maximum measurement density. Human teeth, for example, may only cover a limited region of color space but within the color space the human population is not evenly distributed but tends to cluster in two or more areas. Thus, it typically is more efficient to space tooth shades in an uneven distribution to maximize the acceptance (color match) for a limited number of shades. The option of evenly covering color space while simultaneously shade matching teeth as closely as possible would require using more shades and more restoration materials. Consequently, with typical shade systems there are regions where tooth shades are widely spaced and other regions where tooth shades appear to overlap.

A further complication exists for materials that are translucent and layered and are difficult to quantify. The viewing angle for such materials combined with the angle of the light source relative to the material may affect its returned color spectrum. The construction of the shade tabs also introduces variations in their optical properties. As such, the color of the shade typically is not well known and in certain cases may not be easy to accurately quantify. The uncertainties make it difficult to accurately calculate a ΔE because there is no singular color that represents the shade in all of its representative forms. Rather, the shade must be defined as a region of color space. If the measured material is within the shade region it must be considered as a potential shade match even though it may be far from its reported color resulting in a large ΔE.

Embodiments of the present invention seek to provide a shade matching system/method that desirably utilizes the complementary nature of changes in value and chromacity. Embodiments of the present invention also provide a shade matching system/method that accommodates shades that do not uniformly or evenly cover color space. Embodiments of the present invention also provide a shade matching system/method that accounts for uncertainty in quantifying the color of a shade or in producing a facsimile of the shade.

In accordance with the presently described alternative preferred embodiments of the present invention, each shade in a shade system preferably has assigned to it an L, C and h "color" parameter set (LCh parm) and additionally has a polynomial set that defines a region surrounding the L,C,h parm in three dimensional color space. L and C preferably are defined with a two dimensional closed polygon having up to, for example, 13 vertexes $P_i(L, C)$. Hue preferably is defined with four parameters: $h_{min}$, $h_{low}$, $h_{high}$ and $h_{max}$ where:

$$h_{min} < h_{low} < h_{high} < h_{max}$$

In the hue range $h_{low} < h_{high}$ the L,C polygon preferably has a constant size. In the two hue ranges of $h_{min} < h_{low}$ and $h_{high} < h_{max}$ the L,C polygon preferably decreases linearly in size as h varies from $h_{high}$ to $h_{max}$ and from $h_{low}$ to $h_{min}$. The vertexes of the polygon preferably are scaled relative to the shade L,C,h parm. The scaling factor for decreasing the size of the polygon on the L,C plane in accordance with certain preferred embodiments is:

Scale=0 for $h <= h_{min}$

Scale=$(h-h_{low})/(h_{low}-h_{min})$ for $h_{min} < h < h_{low}$

Scale=1 for $h_{low} <= h <= h_{high}$

Scale=$(h_{high}-h)/(h_{max}-h_{high})$ if $h_{high} < h < h_{max}$

Scale=0 for $h >= h_{max}$

Thus, the polygons as viewed from an L,h or from a C,h plane preferably can have four to six sides. The polygons as viewed from a L,C plane appear as random closed polygons preferably with up to 13 sides. The actual number of vertexes required for each shade typically will vary. Typically six or eight are sufficient to define the color space for a shade set in both the Vita Classical and Vita 3D systems.

Figure 14:
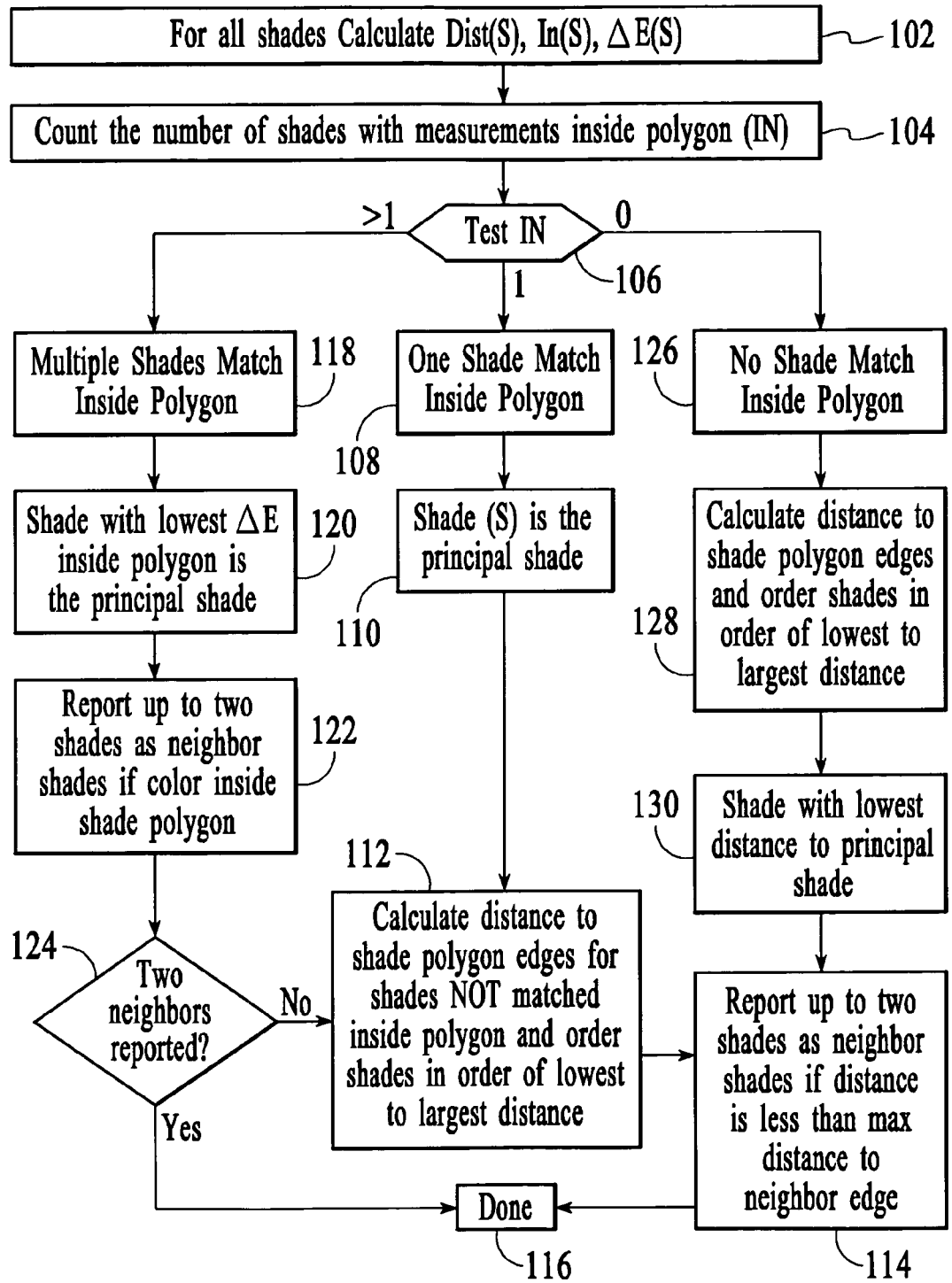

Shade matching proceeds as illustrated in the flow chart of FIG. 14. A measurement of a tooth (or other dental material or other object or material, etc.) is made and L, C, h are determined from the measurement. Each shade is examined to determine if the measured L, C, h is inside or outside of the shade polygon and the distance to the nearest edge (Dist) of the polygon is calculated and stored for each shade (at a minimum, it is preferred that Dist be calculated for each shade for which L, C, h is outside of the polygon for that shade). ΔE of the measurement to each shade's LCh parm preferably is also calculated as discussed above. Thus, in preferred embodiments each shade has three parameters associated with its shade match. Inside the polygon (In), the distance to the nearest edge (Dist) and ΔE.

There are believed to be a number of methods that may be suitable for determining if a point is inside a polygon and any such method may be utilized in the present L,C,h shade matching method. In accordance with preferred embodiments, however, a preferred method is as follows.

Figure 15:
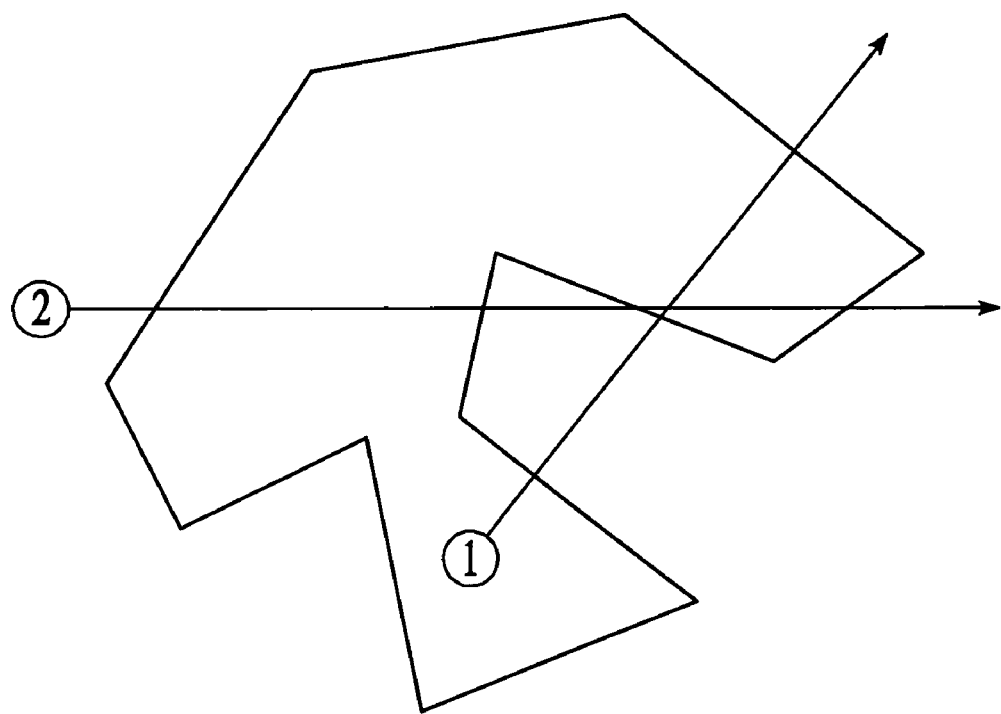

Preferably, each shade polygon is defined with a point queue $Pt_i(x,y)$ where the point queue is a list of the C,L vertexes of the polygon (typically an L,C,h plot proceeds with h as the vertical (z) axis, L as the y axis and C as the x axis). There are N points in the shade point queue where N is the number of vertexes. To determine if a point is inside the two dimensional polygon the number of lines of the polygon that must be crossed when moving in a linear direction to infinity are counted. If the number is even, the point is outside the polygon, if odd the point is inside. Referring to FIG. 15, an example is illustrated to demonstrate this preferred method. Pt 1 is inside a polygon of 11 sides and crosses 3 (odd number) of lines. Pt 2 is outside and crosses 4 lines. Without being bound by theory, the direction of movement does not matter as long as it is in a straight line on the polygon plane.

The algorithm to determine if a point is inside a polygon preferably proceeds as follows. Each line segment of the polygon preferably is examined in the negative x direction (note that any other direction such as positive x or y may also be used). If either of the line segments end points x parms are less than the point x, then the y parms of the line's two end points are examined. If both y end points are greater than or if both are less than the point y, then the line is not crossed. If however the point y is within the lines y end points, then the line may be crossed. To determine if the line may be crossed the x intercept is calculated from the slope of the line and one of its endpoints. If the x intercept is less than the point x the line will be crossed and is counted. The procedure proceeds for all line segments and the number that will be crossed are counted. If an odd number, then the point is inside the polygon; if an even number, then the point is outside the polygon.

Figure 16:
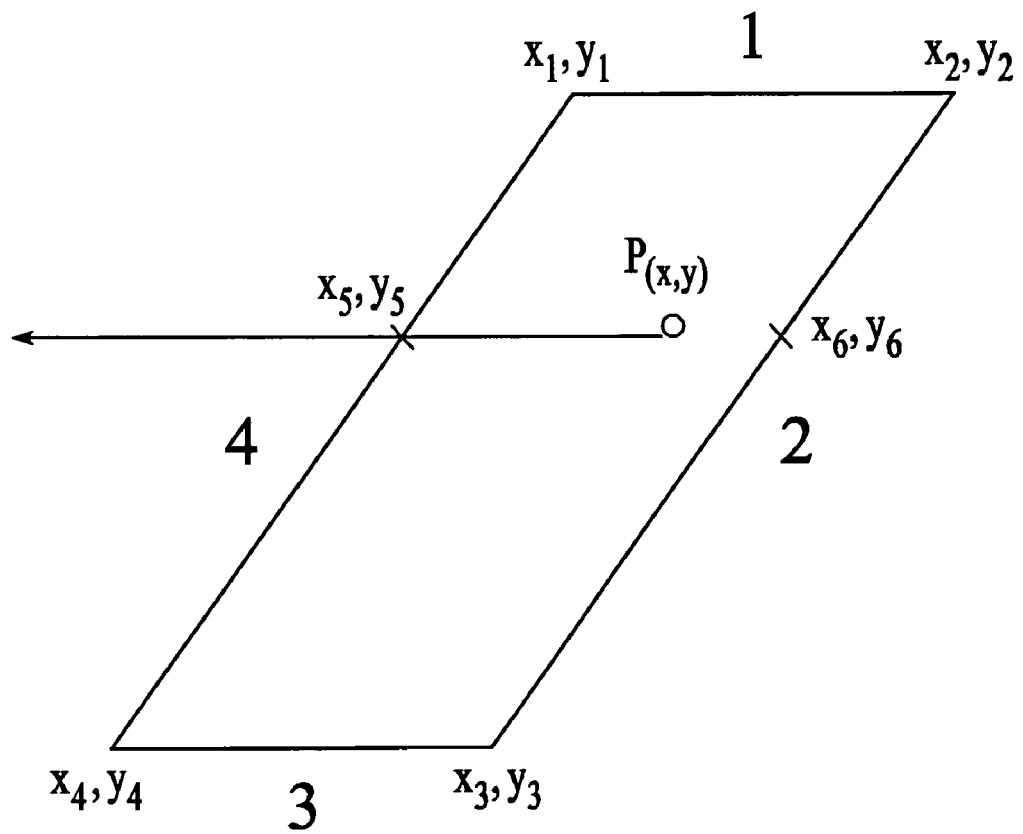

Referring to FIG. 16, a four sided polygon and a point (x,y) inside the polygon are illustrated as a further example. Line segments 1 and 3 have an x ($x_1$ for line 1 and $x_4$ for line 3) that are less than point x but line segment 1 has both y end points greater than point y and line segment 3 has both end points less than point y; accordingly, these two line segments are not crossed. Line segment 2 has y end points that bound point y, but its x intercept ($x_{2,3}$) is greater than point x and is not crossed. Line segment 4 has y end points that bound point y and has an x intercept ($x_{4,1}$) that is less than point x, and thus it is crossed. Since one of the four lines in the polygon of FIG. 3 is crossed point (x,y) is inside the polygon.

In accordance with preferred embodiments, in the three dimensional L,C,h space the vertexes of the L,C polygon preferably are scaled according to the scaling factor described above if h is outside the range of $h_{low}$ to $h_{high}$. If h is outside the range of $h_{min}$ to $h_{max}$, then the polygon preferably is a point (the L,C parm of the shade).

If h is within $h_{min} < h < h_{max}$ and L, C are inside the two dimensional scaled polygon as described above, then the measurement L,C,h preferably is determined to be inside the shade 3-D polygon.

The distance to the polygon preferably is computed as follows. The hue value h is examined. If it is outside the range $h_{min}$ to $h_{max}$, then the distance is the distance between the measurement ($L_M$,$C_M$,$h_M$) and the shade parm ($L_S$,$C_S$, $h_S$):

$$\text{Dist} = \sqrt{(L_M - L_S)^2 + (C_m - C_S)^2 + (h_M - h_{max})^2} \text{ for } h > h_{max}$$

$$\text{Dist} = \sqrt{(L_M - L_S)^2 + (C_m - C_S)^2 + (h_M - h_{min})^2} \text{ for } h < h_{min}$$

If h is inside the range $h_{min}$ to $h_{max}$, then the distance to the polygon edge preferably is calculated by first scaling the LC polygon on the plane of intersection determined by $h_M$ and then calculating the distance to the nearest edge of the polygon on the plane. The distance to the nearest edge preferably is determined by calculating the distance to each polygon line segment and selecting the shortest distance.

Figure 17A:
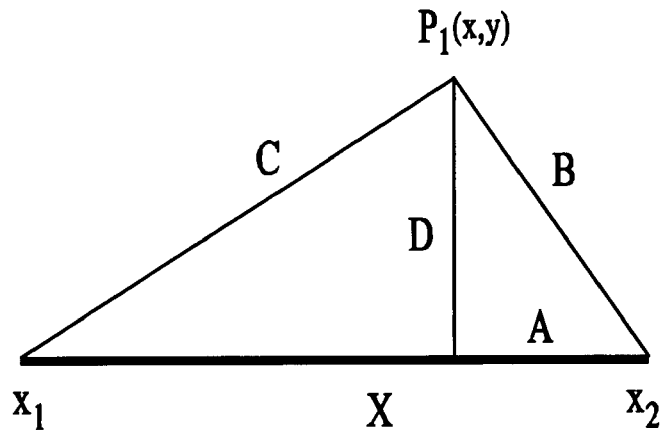
Figure 17B:
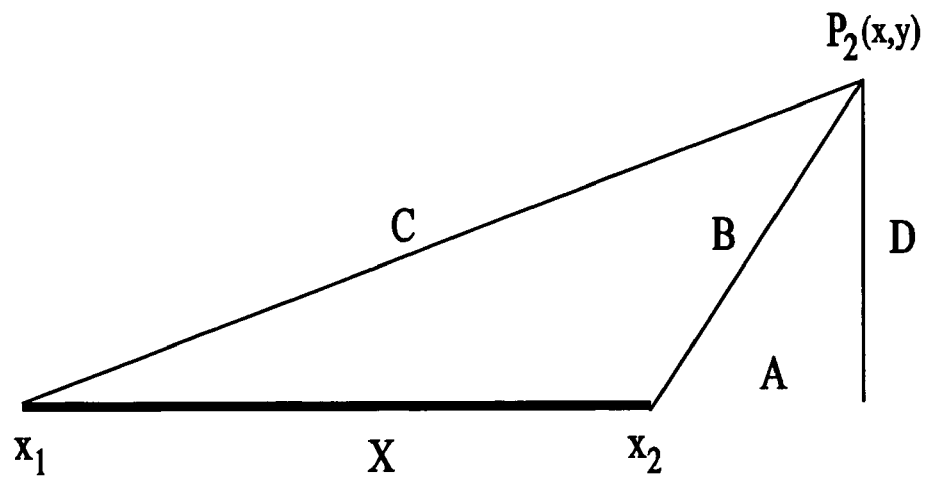

In the preferred embodiment, the distance to a line segment preferably is calculated as illustrated in FIGS. 17A and 17B. The distance preferably is either the perpendicular distance D for point $P_1(x,y)$ or the distance to the nearest line end point B for point $P_2(x,y)$. X is the length of the line segment and is:

$$X = x_2 - x_1$$

B and C are the distances from the ends the line segment to the point (x,y):

$$B = \sqrt{(x - x_2)^2 + y^2}$$

$$C = \sqrt{(x - x_1)^2 + y^2}$$

And C>=B.

If $C^2 > X^2 - B^2$

Then the distance is the line segment B and the point is the point $P_2(x,y)$ illustrated in FIG. 17B.

Otherwise if $C^2 <= X^2 - B^2$

Then the distance is the line segment D illustrated for point $P_1(x,y)$ in FIGS. 17A and D is calculated by:

$$D = \sqrt{C^2 - \{(X^2 + C^2 - B^2)/(2X)\}^2}$$

Referring again to the flow chart of FIG. 14, after calculating the three shade matching parameters In(s), Dist(s) and ΔE(s) for each shade(s), in accordance with preferred embodiments, the preferred shade match is determined as follows:
1) If only one shade has the measurement inside its polygon, then that shade is the preferred shade.
2) If two or more shades have the measurement inside their polygons, then the preferred shade is the shade with the lowest ΔE.
3) If no shades have the measurement inside their polygons, then the preferred shade is the shade with the lowest distance to its polygon edge.

Often a tooth measurement will be near more than one shade. As such and also considering the color variations in a typical tooth and uncertainties in making a color measurement, repeated measurements of an area of a tooth preferably may be utilized in certain alternative embodiments, which could result in the selection of different preferred shades for different measurements. To an unskilled user (or one without sufficient knowledge of how a measurement could be near more than one shade), reporting a different preferred shade—for different measurements may make the instrument appear to be "bouncing around" when in fact the repeated measurements LCh results are changing a small amount (but the small amount of change is sufficient to result in a different preferred shade selection). In certain preferred embodiments, in order to inform a user that a shade match is between shades, the neighbor shades are also reported. In the illustrative preferred embodiment, the neighbor shades preferably are shown in the apparatus main display in a smaller font size as illustrated in FIGS. 18A and 18B. Up to three shades preferably may be shown; in the illustrated embodiment, the preferred shade preferably is shown in a Large font size if there are no neighbors, and in a medium font size if there are neighbors with the neighbor shades shown in a small font.

Preferably, the neighbor shades are determined as follows:
1) If only one shade has the measurement inside its polygon, then it is the preferred shade.
2) If two or more shades have the measurement inside their polygons, then the preferred shade is the shade with the lowest ΔE. The neighbor shades are reported in order of next lowest ΔE, preferably up to two additional shades.
3) If no shades have the measurement inside their polygons, then the preferred shade is the shade with the lowest distance to its polygon edge.
4) If less than two neighbors have been reported in steps 1 to 3 above, then the neighbors preferably are selected if their Dist(s) is less than a predetermined distance and are listed in order of lowest to greatest Dist(s). The predetermined distance may be determined via experiment, for example, and is a distance beyond which the shade is insufficiently close to the shade to be reported as a neighbor (because of visual dissimilarity, etc., to a human observer).

In accordance with certain preferred embodiments, hysteresis also is added to tooth measurements to reduce the appearance of shade matching bounce. In accordance with one such embodiment, if the ΔE of a measurement compared to a previous measurement is less than a predetermined amount (typically a ΔE of 2 or less, which again may be determined by experiment, etc.), then the shade matching result of the former measurement preferably is reported. If the measurement is greater than the pre-determined ΔE, then the new result preferably is reported and the former measurement replaced by the new measurement for future hysteresis comparison.

Also in accordance with preferred embodiments, the Vita 3-D shade system is utilized and can be interpolated for certain 3D shades. Interpolation with a system such as the Vita 3-D shade matching (or similar system) proceeds as follows:
1) If only one shade has the measurement inside its polygon, then that shade is reported in the 3D system.
2) If two or more shades have the measurement inside their shade polygons, then the value and chroma of the reported shade preferably are interpolated by averaging the values and averaging the chromas.
3) Value preferably is reported as the average of the lowest and highest 3D value. (Typically the shade overlap is only one value unit thus value interpolation preferably is 0.5 units only.)
4) Chroma preferably is reported for common hues. If a hue is R or L, then the chroma is averaged for only the R or L shades, and M shades preferably are ignored. (The Vita 3D shade polygons are set such that it is not possible to simultaneously match a R or L shade). If only M shades are matched, then chroma preferably is interpolated for the M shades. Chroma preferably is interpolated by averaging the highest and lowest 3D chroma matches.

It should be noted that for Vita 3D interpolated shades that the polygons for the Vita 3D master system must be arranged for overlap for permitted interpolated 3D shades only, and they must not overlap for shades that may not be interpolated, thereby preventing reporting false 3D interpolated shades.

FIG. 14 will now be described in greater detail. At step 102, a color measurement has been made, and for all shades of the shade system Dist(S), In(S), ΔE(S) are calculated. At step 104, a count is made of the number of shades with the measurement inside the polygon (IN) for each shade. At step 106, the value of In is tested. At step 108, if only one shade has the measurement inside the polygon for that one shade, then at step 110 that shade is determined as the principal shade. The flow then proceeds to step 112, at which a calculation is made of the distance of the measurement to shade polygon edges for shades NOT matched inside polygon, and then the shades preferably are ordered or ranked in order of lowest to largest distance. At step 114, the method preferably consists of reporting up to two shades as neighbor shades if distance is less than max distance to neighbor edge (as previously described, the max distance is a predetermined distance beyond which it is likely that the shade would not be visually close enough to a human observer to be considered a neighboring shade). From step 114, the process basically is complete, as indicated by step 116.

Referring back to step 106, if multiple shades had the measurement inside the polygons of the multiple shades (as indicated by step 118), then the flow proceeds to step 120, at which it preferably is determined that the shade with the lowest ΔE is the principal shade. At step 122, up to two shades preferably are reported as neighbors, with the neighbors being shades for which the measurement was inside the polygon of these shades. Preferably, at step 124, a determination is made if two neighbors were available for reporting at step 122; if no, then the process optionally goes to step 112, at which another neighbor may be identified, and then the two neighbors may be reported at step 114 as before; if at step 124 the desired number (e.g., two) of neighbors were available for reporting at step 122, then the reporting of step 122 preferably is sufficient and the process is complete as indicated by step 116. It should here be noted, however, that the number of neighbors reported, e.g., 0, 1, 2 or other number, are all within the scope of the present invention, and the present invention is not limited to any particular number of reported neighbors.

Referring back to step 106, if no shades had the measurement within the polygons of the shades (as indicated by step 126), then the process proceeds to step 128, at which a calculation is made of the distances of the measurement to shade polygon edges, and preferably the distances are ordered or ranked in order of lowest to largest distance. In preferred embodiments, the shade with the lowest distance is the principal shade, as indicated by step 130. Thereafter, the process preferably proceeds to step 114, at which up to two neighbors may be reported, as before. Thereafter, the process is complete, as indicated by step 116.

As will be apparent from the foregoing description, a primary purpose of the such additional preferred embodiments is to convert mathematical shade systems such as L, C and h tristimulus color coordinates to a more desirable human psychophysiological preferred shade match with a shade system, such as the Vita Classical shade system. In such a system, where the shades are arranged in clusters, there are numerous shades that have very similar tristimulus colors. In such a system, preferential or weighting factors can be created by increasing or decreasing a particular polygon's dimensions to increase or decrease the frequency of a particular shade match result. It has been observed that, with dental shade matching in the Vita Classical system, 40% of all human observers' preferred shade match is an "A" shade result, and specifically, the A2 shade being almost a universal shade. Consequently, the polygon for an A2 shade is quite large to correlate with human observers' preferred shade match. Similar type of weighting factors can be created for the remaining 15 shades.

Also as will be apparent from the foregoing, polygons are used in the preferred embodiments as certain calculations and the like may more readily be carried out with polygons. It should be understood, however, that other geometric or other area constructs may be utilized in accordance with the present invention. What is important is that for the shades in a particular shade system, volumes or regions of color space are created around each shade in a more desired manner, and the volumes or regions are not uniform, but instead are weighted to give more desirable human shade matching results. In particular, the present invention utilizes non-uniform volumes/regions to provide improved shade matching results. In addition, in accordance with embodiments of the present invention for a given hue, for example, the value and chroma dimensions of the volumes/regions may change or vary, and such change or variation may vary from shade to shade. Similarly in accordance with the present invention, alternatively for a given chroma the value and hue dimensions of the volumes/regions may change or vary as described herein, and similarly for a given value the chroma and hue dimensions of the volumes/regions may change or vary as described herein. What is important is that the volumes/regions be optimized for shade matching results that more accurately match human perception based on a given shade system.

It also should be noted that the foregoing polygon-based shade prediction algorithm preferably may be applied with the multi-spectrometer based system previously described. In accordance with the present invention, as previously described data output from one or more spectrometers may parallely collect spectral data, and one or more spectrometer output may be utilized to compute the L, C and h parm set for the measurement. As will be appreciated by those skilled in the art based on the disclosure herein, depending on the class of dental (or other) material being measured (e.g., natural tooth versus PFM restoration), the data output from a single spectrometer may be utilized to compute the L, C and h parm set for the measurement, or the data output from two or more spectrometers may be utilized (such as by averaging or weighted averaging) to compute the L, C and h parm set for the measurement. What is important is that the shade matching algorithm in accordance with the alternative preferred embodiments may be utilized with a single or multi-spectrometer system, although the previous description of a preferred system is utilized in certain embodiments (and the discussion earlier herein of the preferred system, including constructional details, below the critical height measurements, infection prevention barrier, etc., should be understood to be applicable to, but not necessarily required by, the polygon-based shade prediction/reporting methods described herein).

It also should be noted and apparent to those skilled in the art that multiple sets of polygons may also be utilized with multiple spectrometers. One set may for example apply to one spectrometer and another set may apply to another spectrometer. Such combinations of spectrometers and polygons are within the scope of the present invention.

Although the invention has been described in conjunction with specific preferred and other embodiments, it is evident that many substitutions, alternatives and variations will be apparent to those skilled in the art in light of the foregoing description. Accordingly, the invention is intended to embrace all of the alternatives and variations that fall within the spirit and scope of the appended claims. For example, it should be understood that, in accordance with the various alternative embodiments described herein, various systems, and uses and methods based on such systems, may be obtained. The various refinements and alternative and additional features also described may be combined to provide additional advantageous combinations and the like in accordance with the present invention. Also as will be understood by those skilled in the art based on the foregoing description, various aspects of the preferred embodiments may be used in various subcombinations to achieve at least certain of the benefits and attributes described herein, and such subcombinations also are within the scope of the present invention. All such refinements, enhancements and further uses of the present invention are within the scope of the present invention.

What is claimed is:

1. A method for shade matching a dental object and reporting a shade via an output device comprising the steps of:
   determining a polygon in color space for each shade of a plurality of shades in a shade system;
   taking at least one color measurement of the dental object;
   determining if the color measurement of the dental object is within the polygon for each shade of the plurality of shades in the shade system;
   if the color measurement is within the polygon of one shade of the plurality of shades in the shade system, then reporting via the output device the one shade as a principal shade of the dental object;
   if the color measurement is within the polygon of more than one shade of the plurality of shades in the shade system, then reporting via the output device as the principal shade of the dental object a shade of the more than one shade that has a lowest ΔE, wherein the ΔE is calculated for each of the more than one shade based on the color measurement and on a color value for each of the more than one shade; and
   if the color measurement is not within any polygon of any shade of the plurality of shades in the shade system, then reporting via the output device as the principal shade a shade for which the distance between the color measurement in color space and a nearest edge of the polygon for that shade has the lowest value.

2. The method of claim 1, wherein a polygon in color space for a particular shade of the plurality of shades in the shade system is based on complementary changes of value (L) and chromacity (C) of a human observer.

3. The method of claim 1, wherein a polygon in color space for a particular shade of the plurality of shades in the shade system defines value (L) and chromacity (C) parameters for the particular shade.

4. The method of claim 3, wherein a size of the polygon varies based on a hue parameter.

5. The method of claim 1, wherein a set of polygons is determined in color space for each shade of the plurality of shades in the shade system, wherein the set of polygons includes a polygon based on value (L) and chromacity (C), a polygon based on value (L) and hue (h), and a polygon based on chromacity (C) and hue (h), and wherein the set of polygons defines a region of color space for each shade.

6. The method of claim 1, wherein the principal shade is displayed and concurrently with the principle shade, a secondary shade is displayed, wherein the display of the principal shade is displayed differently from the concurrently displayed secondary shade.

7. The method of claim 1, wherein based on the color measurement of the dental object, value (L), chromacity (C) and hue (h) are determined for the dental object.

8. The method of claim 7, wherein a set of polygons is determined in color space for each shade of the plurality of shades in the shade system, wherein the set of polygons includes a polygon based on value (L) and chromacity (C), a polygon based on value (L) and hue (h), and a polygon based on chromacity (C) and hue (h), wherein the set of polygons defines a region of color space for each shade, and wherein for each particular shade, a determination is made of whether the measured L, C and h for the dental object result in the dental object being within the region of color space for that particular shade.

9. The method of claim 8, wherein for each particular shade, a determination is made of a distance between the measured L, C and h for the dental object and a nearest edge of a polygon corresponding to that particular shade.

10. The method of claim 9, wherein for each particular shade, a determination is made of a ΔE between the measured L, C and h for the dental object and that particular shade.

11. A method for shade matching a dental object and reporting a shade via an output device comprising the steps of:
    determining a polygon in color space for each shade of a plurality of shades in a shade system;
    taking at least one color measurement of the dental object;
    determining if the color measurement of the dental object is within the polygon for each shade of the plurality of shades in the shade system;
    if the color measurement is within the polygon of one shade of the plurality of shades in the shade system, then reporting via the output device the one shade as a principal shade of the dental object;
    if the color measurement is within the polygon of more than one shade of the plurality of shades in the shade system, then reporting via the output device as the principal shade of the dental object a shade of the more than one shade that satisfies a first predetermined condition as compared to the remaining shades of the more than one shade, and
    if the color measurement is not within any polygon of any shade of the plurality of shades in the shade system, then reporting via the output device as the principal shade a shade that satisfies a second predetermined condition.

12. The method of claim 11, wherein a polygon in color space for a particular shade of the plurality of shades in the shade system is based on complementary changes of value (L) and chromacity (C) of a human observer.

13. The method of claim 11, wherein a polygon in color space for a particular shade of the plurality shades in the shade system defines value (L) and chromacity (C) parameters for the particular shade.

14. The method of claim 13, wherein a size of the polygon varies based on a hue parameter.

15. The method of claim 11, wherein a set of polygons is determined in color space for each shade of the plurality of shades in the shade system, wherein the set of polygons includes a polygon based on value (L) and chromacity (C), a polygon based on value (L) and hue (h), and a polygon based on chromacity (C) and hue (h), and wherein the set of polygons defines a region of color space for each shade.

16. The method of claim 11, wherein the principal shade is displayed and concurrently a secondary shade is displayed, and wherein the principal shade is displayed differently from the concurrently displayed secondary shade.

17. The method of claim 11, wherein, based on the color measurement of the dental object, value (L), chromacity (C) and hue (h) are determined for the dental object.

18. The method of claim 17, wherein a set of polygons is determined in color space for each shade of the plurality of shades in the shade system, wherein the set of polygons includes a polygon based on value (L) and chromacity (C), a polygon based on value (L) and hue (h), and a polygon based on chromacity (C) and hue (h), wherein the set of polygons defines a region of color space for each shade, and wherein for each particular shade, a determination is made of whether the measured L, C and h for the dental object result in the dental object being within the region of color space for that particular shade.

19. The method of claim 18, wherein for each particular shade, a determination is made of a distance between the measured L, C and h for the dental object and a nearest edge of a polygon corresponding to that particular shade.

20. The method of claim 19, wherein for each particular shade, a determination is made of a $\Delta E$ between the measured L, C and h for the dental object and that particular shade.

* * * * *

UNITED STATES PATENT AND TRADEMARK OFFICE
CERTIFICATE OF CORRECTION

PATENT NO. : 7,301,636 B2  Page 1 of 1
APPLICATION NO. : 10/923647
DATED : November 27, 2007
INVENTOR(S) : Wayne D. Jung It is certified that error appears in the above-identified patent and that said Letters Patent is hereby corrected as shown below:

Column 39, line 66, claim 6     Delete "principle"
                                Insert --principal--

Column 40, line 48, claim 11    After the word "shade",
                                Insert --,--

Signed and Sealed this

Twenty-first Day of October, 2008

JON W. DUDAS
*Director of the United States Patent and Trademark Office*